United States Patent
Körschen et al.

(10) Patent No.: US 7,951,914 B2
(45) Date of Patent: *May 31, 2011

(54) GENETICALLY MODIFIED CYCLIC-NUCLEOTIDE CONTROLLED ION CHANNELS

(75) Inventors: Heinz-Gerd Körschen, Krefeld (DE); Reinhardt Seifert, Jülich (DE); Renate Gauss, Frankfurt (DE); Ulrich Kaupp, Aachen (DE)

(73) Assignee: Forschungszentrum Julich GmbH, Julich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/182,395

(22) Filed: Jul. 30, 2008

(65) Prior Publication Data

US 2009/0104644 A1    Apr. 23, 2009

Related U.S. Application Data

(63) Continuation of application No. 10/486,316, filed as application No. PCT/EP02/08756 on Aug. 6, 2002, now Pat. No. 7,417,117.

(30) Foreign Application Priority Data

Aug. 8, 2001   (DE) .................................. 101 38 876

(51) Int. Cl.
*C07K 14/46*     (2006.01)
*C12N 15/00*    (2006.01)
*C12Q 1/00*     (2006.01)
*C12Q 1/68*     (2006.01)

(52) U.S. Cl. ................ 530/350; 435/4; 435/6; 435/69.1

(58) Field of Classification Search ........................ None
See application file for complete search history.

(56) References Cited

U.S. PATENT DOCUMENTS 7,417,117 B2 *   8/2008   Korschen et al. ............. 530/350
7,547,763 B2     6/2009   Baumann et al. ............. 530/350

OTHER PUBLICATIONS

K.B. Craven; W.N. Zagotta; CNG and HCN Channels . . . ; Annu. Rev. Physiol. 2006.68: 375-401.
E.H. Goulding et al; Molecular Mechanism of Cyclic-nuc . . . ; Letters To Nature, vol. 372; Nov. 24, 1994; 369-374.
M.D. Varnum et al; Molecular Mechanism for Ligands Dis . . . ; Neuron, vol. 15, Sep. 1995; 619-625.
U.B. Kaupp; R. Seifert; Molecular Diversity of Pacemaker Ion . . . ; Annu. Rev. Physiol. 2001, 235-257.
I.T. Weber; T.A. Steitz; Structure of a Complex of Catabolite Gene . . . ; J. Mol. Biol.. 1987;311-326.
W. Altenhofen; J. Ludwig et al; Control of Ligand Specifity . . . ; Proc. Natl. Acad. Sci. 1991; 9868-9872.
J.B. Shabb, B.D. Buzzeo et al; Mutating Protein Kinase cAMP- . . . ; Jour. Bio. Chem. 1991; 24320-24326.
U.B. Kaupp; The Cyclic Nucleotide-gated Channels . . . ; Trends in Neurosciences 1991; 150-157.
J. Ludwig et al; Primary Structure at Cyclic . . . ; FBS Letters; Elsevier Science Pub.; No. 1-2; 1990; 24-29.
U.B. Kaupp et al; Cyclic Nucleotide Gated Ion Ch . . . ; Physiological Reviews; No. 3, Jul. 2002;769-824.

* cited by examiner

*Primary Examiner* — Ruixiang Li
(74) *Attorney, Agent, or Firm* — Jonathan Myers; Andrew Wilford

(57) ABSTRACT

A genetically modified cyclic-nucleotide controlled ion channels where the subunits thereof are altered in such a manner that they have a higher sensitivity for cAMP in relation to cGMP in comparison with the Wildtype according to Seq ID No. 1 and 2.

7 Claims, 20 Drawing Sheets

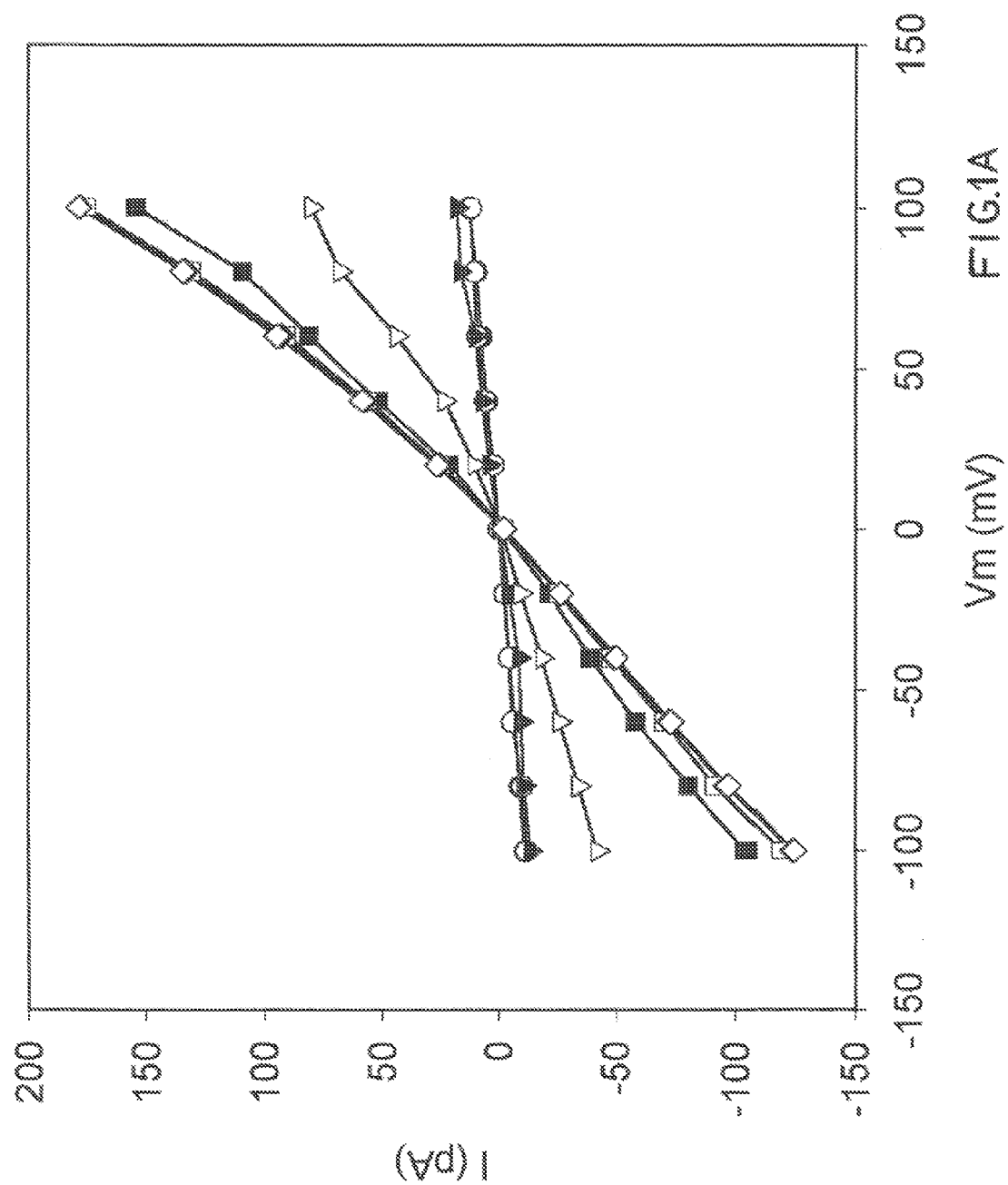

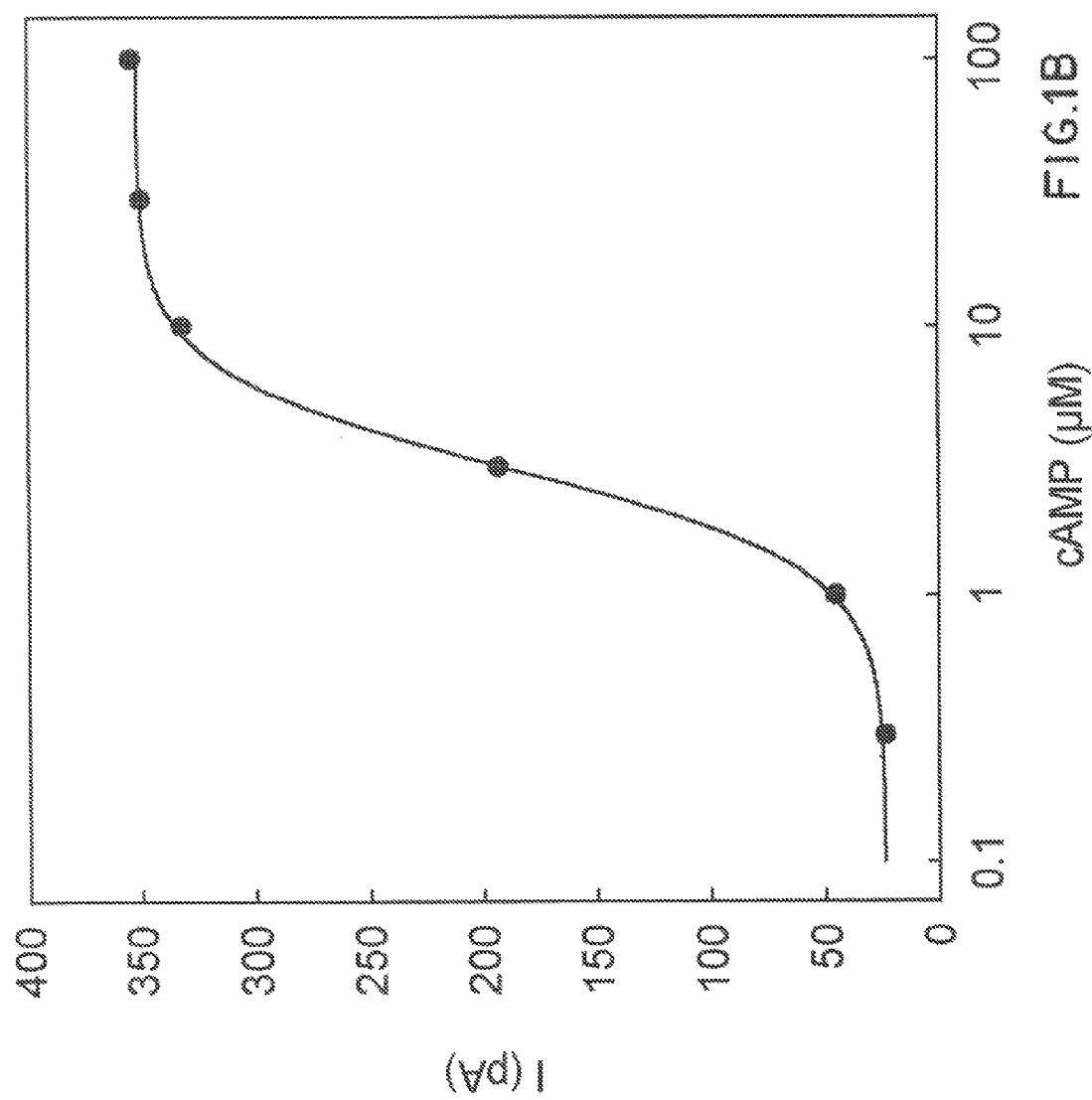

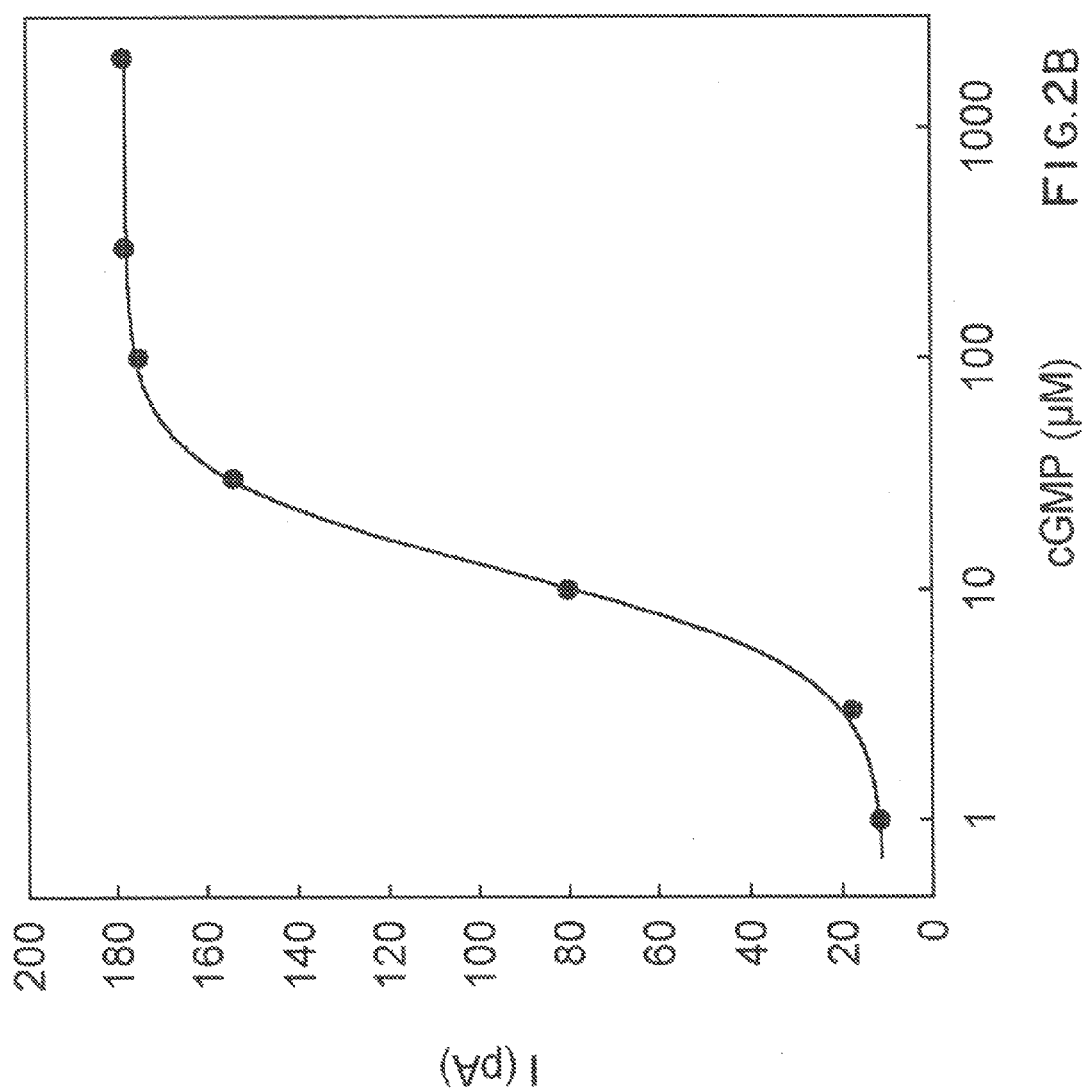

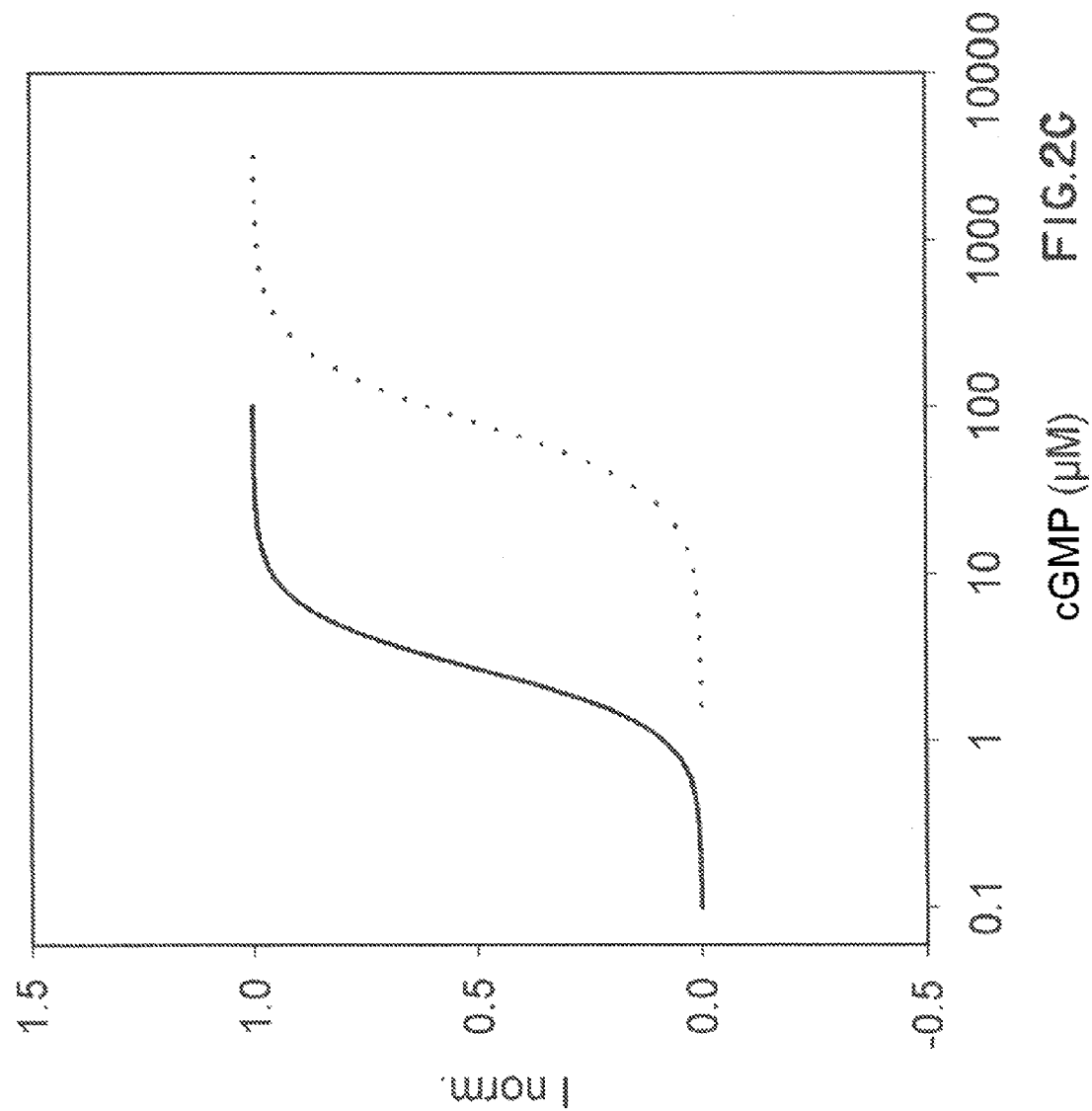

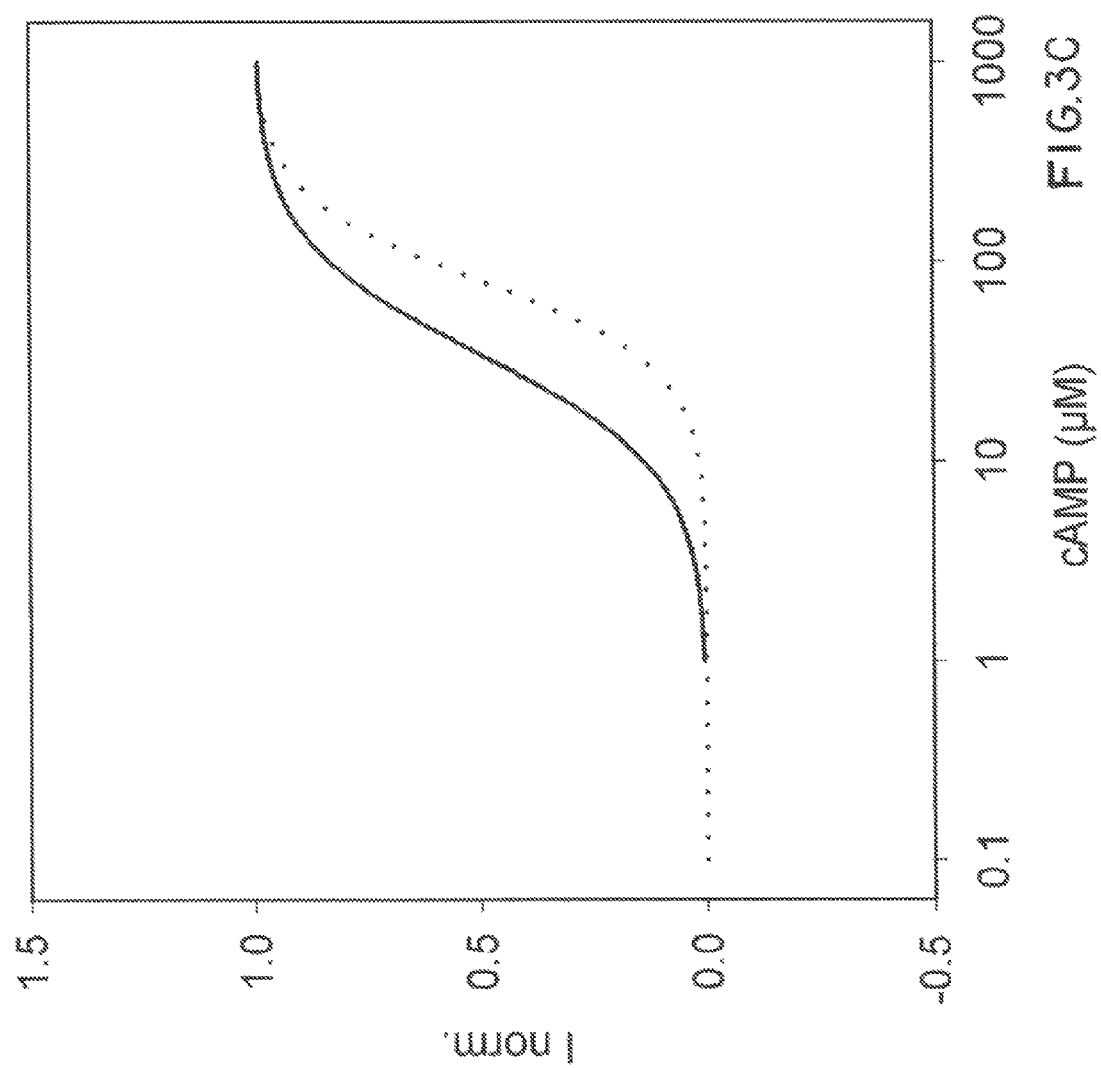

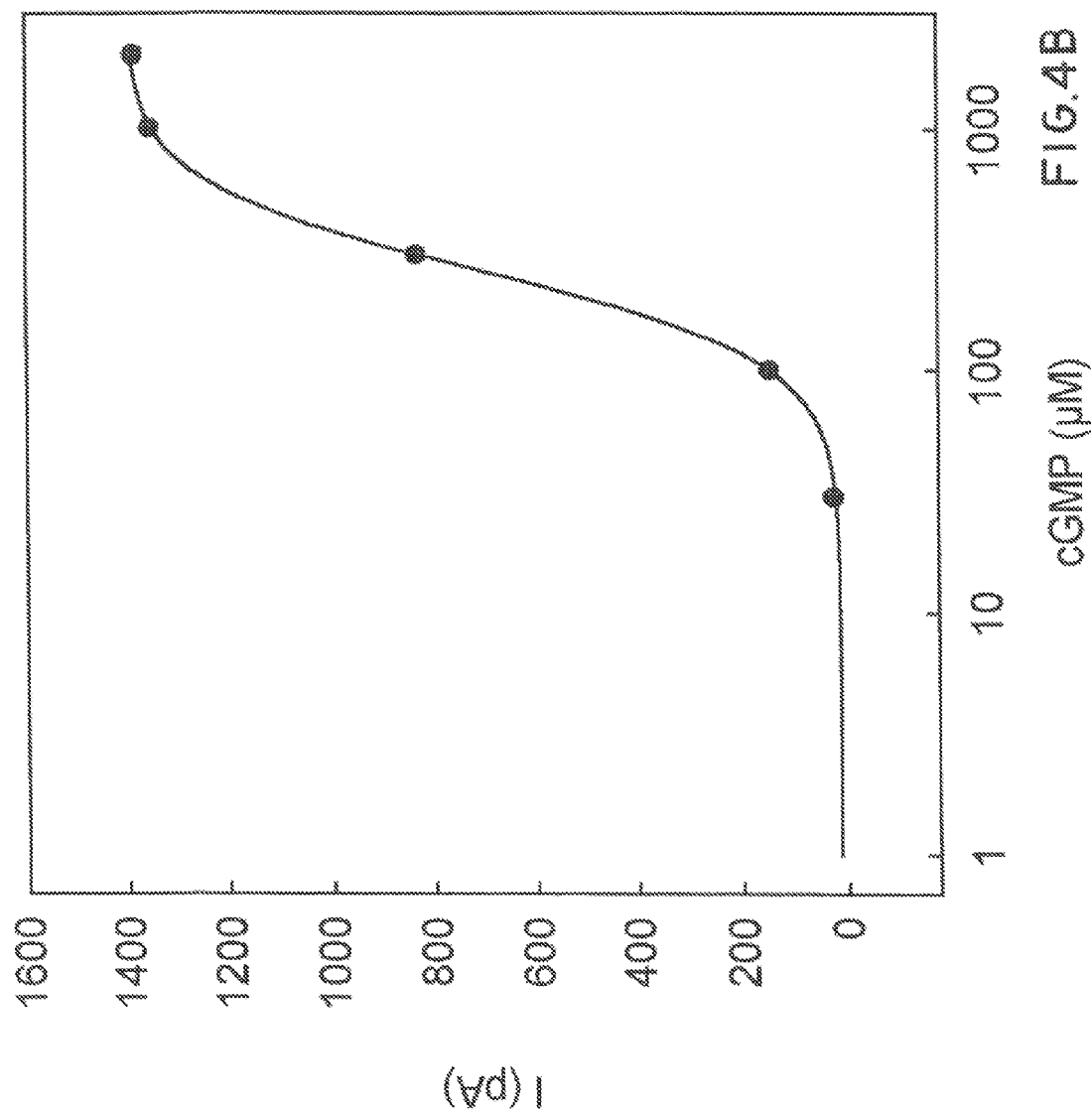

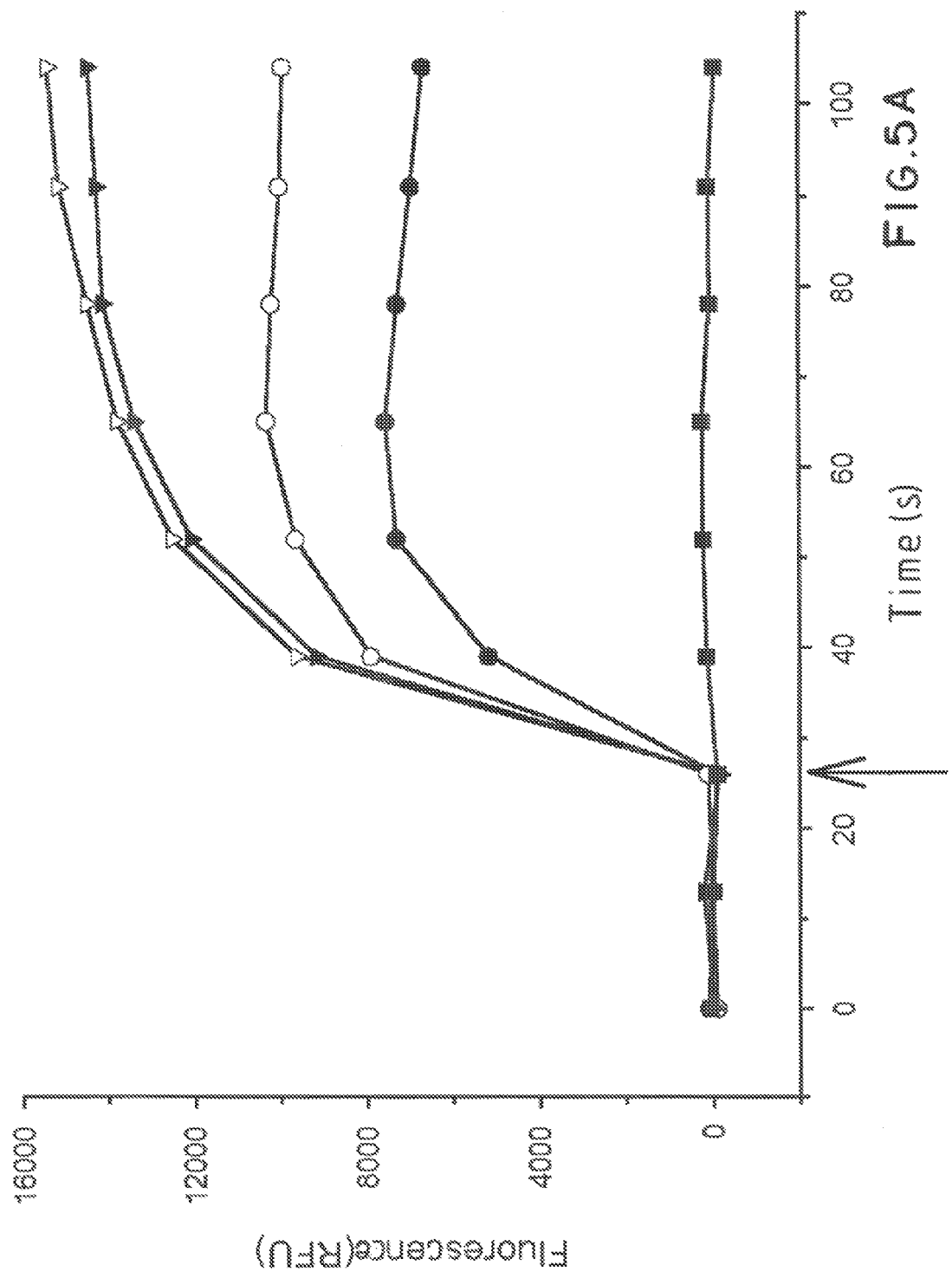

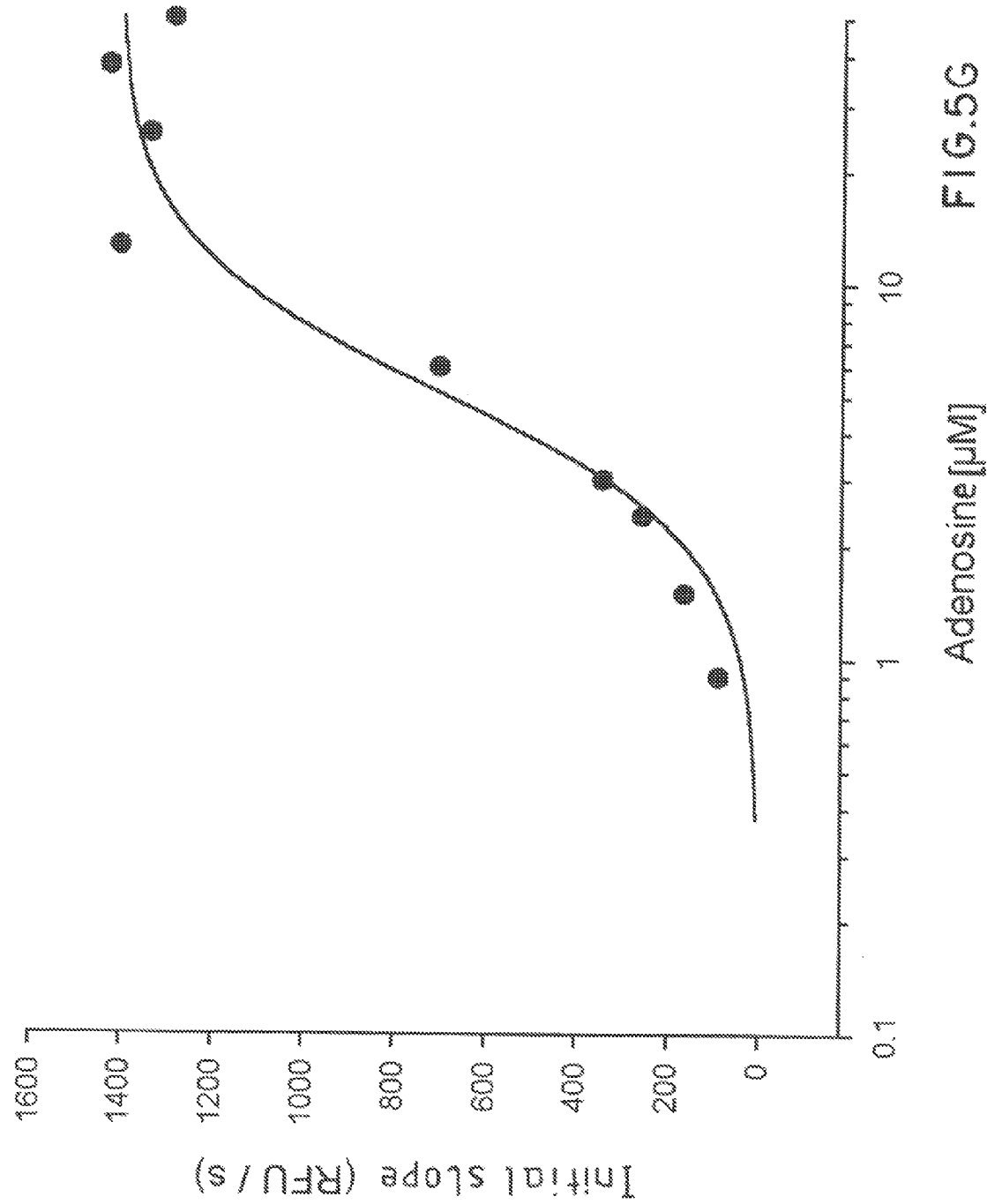

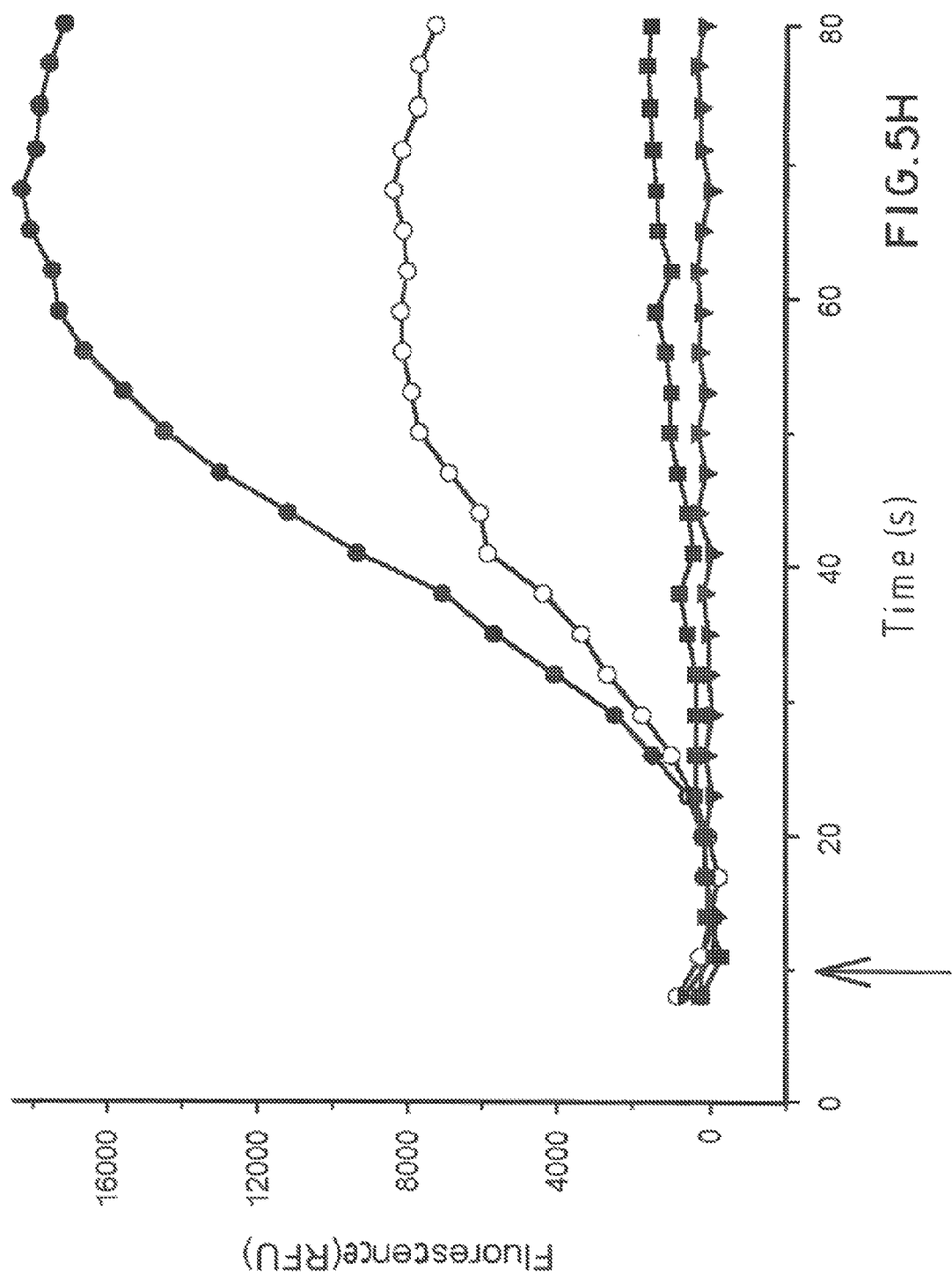

SEQUENCE LISTING

```
<160> NUMBER OF SEQ ID NOS: 12

<210> SEQ ID NO 1
<211> LENGTH: 1989
<212> TYPE: DNA
<213> ORGANISM: Bovine
<220> FEATURE:
<221> NAME/KEY: CDS
<222> LOCATION: (1)..(1989)
<223> OTHER INFORMATION: Nucleic Acid Sequence of the bovine 3-subunit
      of Cyclic Nucleotide-Gated-Ion Channels

<400> SEQUENCE: 1 atg aca gaa aaa gcc aat ggc gtg aag agc tcc cca gcc aat aac cac      48
Met Thr Glu Lys Ala Asn Gly Val Lys Ser Ser Pro Ala Asn Asn His
 1               5                  10                  15 aac cac cat gcc cct cct gcc atc aag gcc agt ggc aaa gat gac cac      96
Asn His His Ala Pro Pro Ala Ile Lys Ala Ser Gly Lys Asp Asp His
             20                  25                  30 agg gcc agc agc cgg cca cag tct gct gct gct gat gac acc tcc tca     144
Arg Ala Ser Ser Arg Pro Gln Ser Ala Ala Ala Asp Asp Thr Ser Ser
         35                  40                  45 gag cta cag caa ctg gca gag atg gat gcc ccc cag cag agg agg ggt     192
Glu Leu Gln Gln Leu Ala Glu Met Asp Ala Pro Gln Gln Arg Arg Gly
     50                  55                  60 ggc ttc cgc agg att gcc cgc ctg gtg ggg gtc ctc aga gag tgg gct     240
Gly Phe Arg Arg Ile Ala Arg Leu Val Gly Val Leu Arg Glu Trp Ala
 65                  70                  75                  80 tac agg aac ttc cgt gag gag gag cct aga cct gac tca ttc ctt gag     288
Tyr Arg Asn Phe Arg Glu Glu Glu Pro Arg Pro Asp Ser Phe Leu Glu
                 85                  90                  95 cgt ttc cgg ggg cct gag ctc cac acc gtg aca aca caa caa gga gac     336
Arg Phe Arg Gly Pro Glu Leu His Thr Val Thr Thr Gln Gln Gly Asp
            100                 105                 110 ggc aaa ggc gac aag gac ggc gag ggc aag ggc acc aag aag aag ttt     384
Gly Lys Gly Asp Lys Asp Gly Glu Gly Lys Gly Thr Lys Lys Lys Phe
        115                 120                 125 gaa ctc ttt gtc ttg gac cca gcc ggg gac tgg tac tac cgc tgg ctt     432
Glu Leu Phe Val Leu Asp Pro Ala Gly Asp Trp Tyr Tyr Arg Trp Leu
    130                 135                 140 ttt ctc att gcc ttg ccc gtc ctc tac aac tgg tgc cta ttg gtg gcc     480
Phe Leu Ile Ala Leu Pro Val Leu Tyr Asn Trp Cys Leu Leu Val Ala
```

```
            145                 150                 155                 160
aga gcc tgc ttc agt gac ctg cag aaa ggc tac tac ata gtg tgg ctg        528
Arg Ala Cys Phe Ser Asp Leu Gln Lys Gly Tyr Tyr Ile Val Trp Leu
                165                 170                 175 gtg ctg gat tac gtc tca gat gtg gtc tac atc gca gac ctc ttc atc        576
Val Leu Asp Tyr Val Ser Asp Val Val Tyr Ile Ala Asp Leu Phe Ile
        180                 185                 190 cga ctg cgc aca ggt ttc ttg gag cag ggg cta ctg gtg aaa gac acc        624
Arg Leu Arg Thr Gly Phe Leu Glu Gln Gly Leu Leu Val Lys Asp Thr
            195                 200                 205 aag aag ttg cgg gac aac tac atc cac acc atg cag ttt aag ctg gat        672
Lys Lys Leu Arg Asp Asn Tyr Ile His Thr Met Gln Phe Lys Leu Asp
210                 215                 220 gtg gcc tcc atc atc cct aca gac ctg atc tat ttt gct gtg ggg atc        720
Val Ala Ser Ile Ile Pro Thr Asp Leu Ile Tyr Phe Ala Val Gly Ile
225                 230                 235                 240 cat aac cct gag gtg cgc ttc aac cgc ctg cta cac ttt gcc cgc atg        768
His Asn Pro Glu Val Arg Phe Asn Arg Leu Leu His Phe Ala Arg Met
                245                 250                 255 ttt gag ttc ttt gac cgc act gag aca cgc acc agc tac ccc aac atc        816
Phe Glu Phe Phe Asp Arg Thr Glu Thr Arg Thr Ser Tyr Pro Asn Ile
        260                 265                 270 ttc cga ata agc aac ctg atc ctc tac atc ttg atc atc cac tgg            864
Phe Arg Ile Ser Asn Leu Ile Leu Tyr Ile Leu Ile Ile His Trp
            275                 280                 285 aat gcc tgc atc tac tat gcc atc tcc aag tcc atc ggc ttt ggg gta        912
Asn Ala Cys Ile Tyr Tyr Ala Ile Ser Lys Ser Ile Gly Phe Gly Val
                290                 295                 300 gac acc tgg gtt tac ccc aac atc act gac cct gag tat ggc tac ctg        960
Asp Thr Trp Val Tyr Pro Asn Ile Thr Asp Pro Glu Tyr Gly Tyr Leu
305                 310                 315                 320 tct agg gag tac atc tat tgc ctt tac tgg tct aca ctg acc ctc acc       1008
Ser Arg Glu Tyr Ile Tyr Cys Leu Tyr Trp Ser Thr Leu Thr Leu Thr
                325                 330                 335 acc att ggg gag aca cca ccc cct gta aag gat gag gag tac ctg ttt       1056
Thr Ile Gly Glu Thr Pro Pro Pro Val Lys Asp Glu Glu Tyr Leu Phe
            340                 345                 350 gtc atc ttt gac ttc ctg att ggt gtc ctc atc ttt gcc acc atc gtg       1104
Val Ile Phe Asp Phe Leu Ile Gly Val Leu Ile Phe Ala Thr Ile Val
        355                 360                 365 gga aat gtg ggc tcc atg atc tcc aac atg aat gcc acc cgg gct gag       1152
Gly Asn Val Gly Ser Met Ile Ser Asn Met Asn Ala Thr Arg Ala Glu
370                 375                 380 ttc cag gcc aag att gat gct gtc aaa cat tat atg cag ttc cga aag       1200
Phe Gln Ala Lys Ile Asp Ala Val Lys His Tyr Met Gln Phe Arg Lys
385                 390                 395                 400 gtc agc aag gag atg gaa gcc aag gtc att agg tgg ttt gac tac ttg       1248
Val Ser Lys Glu Met Glu Ala Lys Val Ile Arg Trp Phe Asp Tyr Leu
                405                 410                 415 tgg acc aat aag aag agt gta gat gag cga gaa gtc ctc aaa aac ctg       1296
Trp Thr Asn Lys Lys Ser Val Asp Glu Arg Glu Val Leu Lys Asn Leu
            420                 425                 430 cca gca aag ctc agg gct gag ata gcc atc aac gtc cac ctg tcc aca       1344
Pro Ala Lys Leu Arg Ala Glu Ile Ala Ile Asn Val His Leu Ser Thr
                435                 440                 445 ctc aag aaa gtg cgc atc ttt cag gac tgt gag gct ggc ctg ctg gtg       1392
Leu Lys Lys Val Arg Ile Phe Gln Asp Cys Glu Ala Gly Leu Leu Val
        450                 455                 460 gaa ctg gta tta aag ctc cgg cct cag gtc ttt agc cct ggg gac tac       1440
Glu Leu Val Leu Lys Leu Arg Pro Gln Val Phe Ser Pro Gly Asp Tyr
```

-continued

```
                465                 470                 475                 480
att tgc cgc aag ggg gat att ggg aag gag atg tac ata atc aag gag      1488
Ile Cys Arg Lys Gly Asp Ile Gly Lys Glu Met Tyr Ile Ile Lys Glu
                485                 490                 495 gga aaa ttg gca gtg gtg gct gat gac ggt gtc act cag tat gcc ctg      1536
Gly Lys Leu Ala Val Val Ala Asp Asp Gly Val Thr Gln Tyr Ala Leu
            500                 505                 510 ctc tcg gct ggg agt tgc ttt gga gag atc agt atc ctt aat att aag      1584
Leu Ser Ala Gly Ser Cys Phe Gly Glu Ile Ser Ile Leu Asn Ile Lys
        515                 520                 525 ggc agc aaa atg ggc aat cgg cgc aca gcc aac atc cgc agt ctt ggc      1632
Gly Ser Lys Met Gly Asn Arg Arg Thr Ala Asn Ile Arg Ser Leu Gly
    530                 535                 540 tac tct gat ctg ttc tgc ttg tcc aag gat gat ctt atg gaa gct gtg      1680
Tyr Ser Asp Leu Phe Cys Leu Ser Lys Asp Asp Leu Met Glu Ala Val
545                 550                 555                 560 act gag tac cct gat gcc aag agg gtc ttg gag gag aga ggc cgg gag      1728
Thr Glu Tyr Pro Asp Ala Lys Arg Val Leu Glu Glu Arg Gly Arg Glu
                565                 570                 575 att ctg atg aag gag ggc ttg ttg gat gag aat gag gtg gca gcc agc      1776
Ile Leu Met Lys Glu Gly Leu Leu Asp Glu Asn Glu Val Ala Ala Ser
            580                 585                 590 atg gag gta gat gtg cag gaa aag cta gaa cag ctg gag acc aac atg      1824
Met Glu Val Asp Val Gln Glu Lys Leu Glu Gln Leu Glu Thr Asn Met
        595                 600                 605 gac acc ttg tac act cgt ttt gcc cgc ctg ctg gcc gag tac acg gga      1872
Asp Thr Leu Tyr Thr Arg Phe Ala Arg Leu Leu Ala Glu Tyr Thr Gly
    610                 615                 620 gcc cag cag aag ctc aag cag cgc atc aca gtt ttg gaa acg aag atg      1920
Ala Gln Gln Lys Leu Lys Gln Arg Ile Thr Val Leu Glu Thr Lys Met
625                 630                 635                 640 aag cag aat aat gag gat gac tcc ctg tca gat ggg atg aac agc cca      1968
Lys Gln Asn Asn Glu Asp Asp Ser Leu Ser Asp Gly Met Asn Ser Pro
                645                 650                 655 gag cca cct gcc gag aag cca                                          1989
Glu Pro Pro Ala Glu Lys Pro
            660
```

<210> SEQ ID NO 2
<211> LENGTH: 663
<212> TYPE: PRT
<213> ORGANISM: Bovine

<400> SEQUENCE: 2

```
Met Thr Glu Lys Ala Asn Gly Val Lys Ser Ser Pro Ala Asn Asn His
  1               5                  10                  15

Asn His His Ala Pro Pro Ala Ile Lys Ala Ser Gly Lys Asp Asp His
                 20                  25                  30

Arg Ala Ser Ser Arg Pro Gln Ser Ala Ala Asp Asp Thr Ser Ser
             35                  40                  45

Glu Leu Gln Gln Leu Ala Glu Met Asp Ala Pro Gln Gln Arg Arg Gly
         50                  55                  60

Gly Phe Arg Arg Ile Ala Arg Leu Val Gly Val Leu Arg Glu Trp Ala
 65                  70                  75                  80

Tyr Arg Asn Phe Arg Glu Glu Pro Arg Pro Asp Ser Phe Leu Glu
                 85                  90                  95

Arg Phe Arg Gly Pro Glu Leu His Thr Val Thr Thr Gln Gln Gly Asp
            100                 105                 110

Gly Lys Gly Asp Lys Asp Gly Glu Gly Lys Gly Thr Lys Lys Lys Phe
```

-continued

```
            115                 120                 125
Glu Leu Phe Val Leu Asp Pro Ala Gly Asp Trp Tyr Tyr Arg Trp Leu
        130                 135                 140
Phe Leu Ile Ala Leu Pro Val Leu Tyr Asn Trp Cys Leu Leu Val Ala
145                 150                 155                 160
Arg Ala Cys Phe Ser Asp Leu Gln Lys Gly Tyr Tyr Ile Val Trp Leu
                165                 170                 175
Val Leu Asp Tyr Val Ser Asp Val Val Tyr Ile Ala Asp Leu Phe Ile
            180                 185                 190
Arg Leu Arg Thr Gly Phe Leu Glu Gln Gly Leu Leu Val Lys Asp Thr
        195                 200                 205
Lys Lys Leu Arg Asp Asn Tyr Ile His Thr Met Gln Phe Lys Leu Asp
210                 215                 220
Val Ala Ser Ile Ile Pro Thr Asp Leu Ile Tyr Phe Ala Val Gly Ile
225                 230                 235                 240
His Asn Pro Glu Val Arg Phe Asn Arg Leu Leu His Phe Ala Arg Met
                245                 250                 255
Phe Glu Phe Phe Asp Arg Thr Glu Thr Arg Thr Ser Tyr Pro Asn Ile
            260                 265                 270
Phe Arg Ile Ser Asn Leu Ile Leu Tyr Ile Leu Ile Ile His Trp
        275                 280                 285
Asn Ala Cys Ile Tyr Tyr Ala Ile Ser Lys Ser Ile Gly Phe Gly Val
290                 295                 300
Asp Thr Trp Val Tyr Pro Asn Ile Thr Asp Pro Glu Tyr Gly Tyr Leu
305                 310                 315                 320
Ser Arg Glu Tyr Ile Tyr Cys Leu Tyr Trp Ser Thr Leu Thr Leu Thr
                325                 330                 335
Thr Ile Gly Glu Thr Pro Pro Pro Val Lys Asp Glu Glu Tyr Leu Phe
            340                 345                 350
Val Ile Phe Asp Phe Leu Ile Gly Val Leu Ile Phe Ala Thr Ile Val
        355                 360                 365
Gly Asn Val Gly Ser Met Ile Ser Asn Met Asn Ala Thr Arg Ala Glu
370                 375                 380
Phe Gln Ala Lys Ile Asp Ala Val Lys His Tyr Met Gln Phe Arg Lys
385                 390                 395                 400
Val Ser Lys Glu Met Glu Ala Lys Val Ile Arg Trp Phe Asp Tyr Leu
                405                 410                 415
Trp Thr Asn Lys Lys Ser Val Asp Glu Arg Glu Val Leu Lys Asn Leu
            420                 425                 430
Pro Ala Lys Leu Arg Ala Glu Ile Ala Ile Asn Val His Leu Ser Thr
        435                 440                 445
Leu Lys Lys Val Arg Ile Phe Gln Asp Cys Glu Ala Gly Leu Leu Val
450                 455                 460
Glu Leu Val Leu Lys Leu Arg Pro Gln Val Phe Ser Pro Gly Asp Tyr
465                 470                 475                 480
Ile Cys Arg Lys Gly Asp Ile Gly Lys Glu Met Tyr Ile Ile Lys Glu
                485                 490                 495
Gly Lys Leu Ala Val Val Ala Asp Asp Gly Val Thr Gln Tyr Ala Leu
            500                 505                 510
Leu Ser Ala Gly Ser Cys Phe Gly Glu Ile Ser Ile Leu Asn Ile Lys
        515                 520                 525
Gly Ser Lys Met Gly Asn Arg Arg Thr Ala Asn Ile Arg Ser Leu Gly
530                 535                 540
```

```
Tyr Ser Asp Leu Phe Cys Leu Ser Lys Asp Asp Leu Met Glu Ala Val
545                 550                 555                 560

Thr Glu Tyr Pro Asp Ala Lys Arg Val Leu Glu Glu Arg Gly Arg Glu
                565                 570                 575

Ile Leu Met Lys Glu Gly Leu Leu Asp Glu Asn Glu Val Ala Ala Ser
            580                 585                 590

Met Glu Val Asp Val Gln Glu Lys Leu Glu Gln Leu Glu Thr Asn Met
        595                 600                 605

Asp Thr Leu Tyr Thr Arg Phe Ala Arg Leu Leu Ala Glu Tyr Thr Gly
    610                 615                 620

Ala Gln Gln Lys Leu Lys Gln Arg Ile Thr Val Leu Glu Thr Lys Met
625                 630                 635                 640

Lys Gln Asn Asn Glu Asp Asp Ser Leu Ser Asp Gly Met Asn Ser Pro
                645                 650                 655

Glu Pro Pro Ala Glu Lys Pro
            660

<210> SEQ ID NO 3
<211> LENGTH: 1989
<212> TYPE: DNA
<213> ORGANISM: Bovine
<220> FEATURE:
<221> NAME/KEY: CDS
<222> LOCATION: (1)..(1989)
<223> OTHER INFORMATION: Nucleic Acid Sequence of genetically modified
      bovine T537M- 3-subunit of cyclic nucleotide gated-ion channels

<400> SEQUENCE: 3 atg aca gaa aaa gcc aat ggc gtg aag agc tcc cca gcc aat aac cac      48
Met Thr Glu Lys Ala Asn Gly Val Lys Ser Ser Pro Ala Asn Asn His
1               5                   10                  15 aac cac cat gcc cct cct gcc atc aag gcc agt ggc aaa gat gac cac      96
Asn His His Ala Pro Pro Ala Ile Lys Ala Ser Gly Lys Asp Asp His
            20                  25                  30 agg gcc agc agc cgg cca cag tct gct gct gct gat gac acc tcc tca      144
Arg Ala Ser Ser Arg Pro Gln Ser Ala Ala Ala Asp Asp Thr Ser Ser
        35                  40                  45 gag cta cag caa ctg gca gag atg gat gcc ccc cag cag agg agg ggt      192
Glu Leu Gln Gln Leu Ala Glu Met Asp Ala Pro Gln Gln Arg Arg Gly
    50                  55                  60 ggc ttc cgc agg att gcc cgc ctg gtg ggg gtc ctc aga gag tgg gct      240
Gly Phe Arg Arg Ile Ala Arg Leu Val Gly Val Leu Arg Glu Trp Ala
65                  70                  75                  80 tac agg aac ttc cgt gag gag gag cct aga cct gac tca ttc ctt gag      288
Tyr Arg Asn Phe Arg Glu Glu Glu Pro Arg Pro Asp Ser Phe Leu Glu
                85                  90                  95 cgt ttc cgg ggg cct gag ctc cac acc gtg aca aca caa caa gga gac      336
Arg Phe Arg Gly Pro Glu Leu His Thr Val Thr Thr Gln Gln Gly Asp
            100                 105                 110 ggc aaa ggc gac aag gac ggc gag ggc aag ggc acc aag aag aag ttt      384
Gly Lys Gly Asp Lys Asp Gly Glu Gly Lys Gly Thr Lys Lys Lys Phe
        115                 120                 125 gaa ctc ttt gtc ttg gac cca gcc ggg gac tgg tac tac cgc tgg ctt      432
Glu Leu Phe Val Leu Asp Pro Ala Gly Asp Trp Tyr Tyr Arg Trp Leu
    130                 135                 140 ttt ctc att gcc ttg ccc gtc ctc tac aac tgg tgc cta ttg gtg gcc      480
Phe Leu Ile Ala Leu Pro Val Leu Tyr Asn Trp Cys Leu Leu Val Ala
145                 150                 155                 160 aga gcc tgc ttc agt gac ctg cag aaa ggc tac tac ata gtg tgg ctg      528
Arg Ala Cys Phe Ser Asp Leu Gln Lys Gly Tyr Tyr Ile Val Trp Leu
                165                 170                 175
```

```
gtg ctg gat tac gtc tca gat gtg gtc tac atc gca gac ctc ttc atc      576
Val Leu Asp Tyr Val Ser Asp Val Val Tyr Ile Ala Asp Leu Phe Ile
            180             185             190 cga ctg cgc aca ggt ttc ttg gag cag ggg cta ctg gtg aaa gac acc      624
Arg Leu Arg Thr Gly Phe Leu Glu Gln Gly Leu Leu Val Lys Asp Thr
            195             200             205 aag aag ttg cgg gac aac tac atc cac acc atg cag ttt aag ctg gat      672
Lys Lys Leu Arg Asp Asn Tyr Ile His Thr Met Gln Phe Lys Leu Asp
            210             215             220 gtg gcc tcc atc atc cct aca gac ctg atc tat ttt gct gtg ggg atc      720
Val Ala Ser Ile Ile Pro Thr Asp Leu Ile Tyr Phe Ala Val Gly Ile
225             230             235             240 cat aac cct gag gtg cgc ttc aac cgc ctg cta cac ttt gcc cgc atg      768
His Asn Pro Glu Val Arg Phe Asn Arg Leu Leu His Phe Ala Arg Met
            245             250             255 ttt gag ttc ttt gac cgc act gag aca cgc acc agc tac ccc aac atc      816
Phe Glu Phe Phe Asp Arg Thr Glu Thr Arg Thr Ser Tyr Pro Asn Ile
            260             265             270 ttc cga ata agc aac ctg atc ctc tac atc ttg atc atc att cac tgg      864
Phe Arg Ile Ser Asn Leu Ile Leu Tyr Ile Leu Ile Ile His Trp
            275             280             285 aat gcc tgc atc tac tat gcc atc tcc aag tcc atc ggc ttt ggg gta      912
Asn Ala Cys Ile Tyr Tyr Ala Ile Ser Lys Ser Ile Gly Phe Gly Val
            290             295             300 gac acc tgg gtt tac ccc aac atc act gac cct gag tat ggc tac ctg      960
Asp Thr Trp Val Tyr Pro Asn Ile Thr Asp Pro Glu Tyr Gly Tyr Leu
305             310             315             320 tct agg gag tac atc tat tgc ctt tac tgg tct aca ctg acc ctc acc     1008
Ser Arg Glu Tyr Ile Tyr Cys Leu Tyr Trp Ser Thr Leu Thr Leu Thr
            325             330             335 acc att ggg gag aca cca ccc cct gta aag gat gag gag tac ctg ttt     1056
Thr Ile Gly Glu Thr Pro Pro Pro Val Lys Asp Glu Glu Tyr Leu Phe
            340             345             350 gtc atc ttt gac ttc ctg att ggt gtc ctc atc ttt gcc acc atc gtg     1104
Val Ile Phe Asp Phe Leu Ile Gly Val Leu Ile Phe Ala Thr Ile Val
            355             360             365 gga aat gtg ggc tcc atg atc tcc aac atg aat gcc acc cgg gct gag     1152
Gly Asn Val Gly Ser Met Ile Ser Asn Met Asn Ala Thr Arg Ala Glu
            370             375             380 ttc cag gcc aag att gat gct gtc aaa cat tat atg cag ttc cga aag     1200
Phe Gln Ala Lys Ile Asp Ala Val Lys His Tyr Met Gln Phe Arg Lys
385             390             395             400 gtc agc aag gag atg gaa gcc aag gtc att agg tgg ttt gac tac ttg     1248
Val Ser Lys Glu Met Glu Ala Lys Val Ile Arg Trp Phe Asp Tyr Leu
            405             410             415 tgg acc aat aag aag agt gta gat gag cga gaa gtc ctc aaa aac ctg     1296
Trp Thr Asn Lys Lys Ser Val Asp Glu Arg Glu Val Leu Lys Asn Leu
            420             425             430 cca gca aag ctc agg gct gag ata gcc atc aac gtc cac ctg tcc aca     1344
Pro Ala Lys Leu Arg Ala Glu Ile Ala Ile Asn Val His Leu Ser Thr
            435             440             445 ctc aag aaa gtg cgc atc ttt cag gac tgt gag gct ggc ctg ctg gtg     1392
Leu Lys Lys Val Arg Ile Phe Gln Asp Cys Glu Ala Gly Leu Leu Val
450             455             460 gaa ctg gta tta aag ctc cgg cct cag gtc ttt agc cct ggg gac tac     1440
Glu Leu Val Leu Lys Leu Arg Pro Gln Val Phe Ser Pro Gly Asp Tyr
465             470             475             480 att tgc cgc aag ggg gat att ggg aag gag atg tac ata atc aag gag     1488
Ile Cys Arg Lys Gly Asp Ile Gly Lys Glu Met Tyr Ile Ile Lys Glu
            485             490             495
```

```
gga aaa ttg gca gtg gtg gct gat gac ggt gtc act cag tat gcc ctg      1536
Gly Lys Leu Ala Val Val Ala Asp Asp Gly Val Thr Gln Tyr Ala Leu
            500                 505                 510 ctc tcg gct ggg agt tgc ttt gga gag atc agt atc ctt aat att aag      1584
Leu Ser Ala Gly Ser Cys Phe Gly Glu Ile Ser Ile Leu Asn Ile Lys
            515                 520                 525 ggc agc aaa atg ggc aat cgg cgc atg gcc aac atc cgc agt ctt ggc      1632
Gly Ser Lys Met Gly Asn Arg Arg Met Ala Asn Ile Arg Ser Leu Gly
            530                 535                 540 tac tct gat ctg ttc tgc ttg tcc aag gat gat ctt atg gaa gct gtg      1680
Tyr Ser Asp Leu Phe Cys Leu Ser Lys Asp Asp Leu Met Glu Ala Val
545                 550                 555                 560 act gag tac cct gat gcc aag agg gtc ttg gag gag aga ggc cgg gag      1728
Thr Glu Tyr Pro Asp Ala Lys Arg Val Leu Glu Glu Arg Gly Arg Glu
                565                 570                 575 att ctg atg aag gag ggc ttg ttg gat gag aat gag gtg gca gcc agc      1776
Ile Leu Met Lys Glu Gly Leu Leu Asp Glu Asn Glu Val Ala Ala Ser
            580                 585                 590 atg gag gta gat gtg cag gaa aag cta gaa cag ctg gag acc aac atg      1824
Met Glu Val Asp Val Gln Glu Lys Leu Glu Gln Leu Glu Thr Asn Met
            595                 600                 605 gac acc ttg tac act cgt ttt gcc cgc ctg ctg gcc gag tac acg gga      1872
Asp Thr Leu Tyr Thr Arg Phe Ala Arg Leu Leu Ala Glu Tyr Thr Gly
610                 615                 620 gcc cag cag aag ctc aag cag cgc atc aca gtt ttg gaa acg aag atg      1920
Ala Gln Gln Lys Leu Lys Gln Arg Ile Thr Val Leu Glu Thr Lys Met
625                 630                 635                 640 aag cag aat aat gag gat gac tcc ctg tca gat ggg atg aac agc cca      1968
Lys Gln Asn Asn Glu Asp Asp Ser Leu Ser Asp Gly Met Asn Ser Pro
                645                 650                 655 gag cca cct gcc gag aag cca                                          1989
Glu Pro Pro Ala Glu Lys Pro
            660

<210> SEQ ID NO 4
<211> LENGTH: 663
<212> TYPE: PRT
<213> ORGANISM: Bovine

<400> SEQUENCE: 4

Met Thr Glu Lys Ala Asn Gly Val Lys Ser Ser Pro Ala Asn Asn His
  1               5                  10                  15

Asn His His Ala Pro Pro Ala Ile Lys Ala Ser Gly Lys Asp Asp His
             20                  25                  30

Arg Ala Ser Ser Arg Pro Gln Ser Ala Ala Asp Asp Thr Ser Ser
         35                  40                  45

Glu Leu Gln Gln Leu Ala Glu Met Asp Ala Pro Gln Gln Arg Arg Gly
     50                  55                  60

Gly Phe Arg Arg Ile Ala Arg Leu Val Gly Val Leu Arg Glu Trp Ala
 65                  70                  75                  80

Tyr Arg Asn Phe Arg Glu Glu Pro Arg Pro Asp Ser Phe Leu Glu
             85                  90                  95

Arg Phe Arg Gly Pro Glu Leu His Thr Val Thr Thr Gln Gln Gly Asp
            100                 105                 110

Gly Lys Gly Asp Lys Asp Gly Glu Gly Lys Gly Thr Lys Lys Phe
        115                 120                 125

Glu Leu Phe Val Leu Asp Pro Ala Gly Asp Trp Tyr Tyr Arg Trp Leu
    130                 135                 140
```

```
Phe Leu Ile Ala Leu Pro Val Leu Tyr Asn Trp Cys Leu Val Ala
145                 150                 155                 160

Arg Ala Cys Phe Ser Asp Leu Gln Lys Gly Tyr Tyr Ile Val Trp Leu
                165                 170                 175

Val Leu Asp Tyr Val Ser Asp Val Val Tyr Ile Ala Asp Leu Phe Ile
            180                 185                 190

Arg Leu Arg Thr Gly Phe Leu Glu Gln Gly Leu Leu Val Lys Asp Thr
        195                 200                 205

Lys Lys Leu Arg Asp Asn Tyr Ile His Thr Met Gln Phe Lys Leu Asp
    210                 215                 220

Val Ala Ser Ile Ile Pro Thr Asp Leu Ile Tyr Phe Ala Val Gly Ile
225                 230                 235                 240

His Asn Pro Glu Val Arg Phe Asn Arg Leu Leu His Phe Ala Arg Met
                245                 250                 255

Phe Glu Phe Phe Asp Arg Thr Glu Thr Arg Thr Ser Tyr Pro Asn Ile
                260                 265                 270

Phe Arg Ile Ser Asn Leu Ile Leu Tyr Ile Leu Ile Ile His Trp
        275                 280                 285

Asn Ala Cys Ile Tyr Tyr Ala Ile Ser Lys Ser Ile Gly Phe Gly Val
    290                 295                 300

Asp Thr Trp Val Tyr Pro Asn Ile Thr Asp Pro Glu Tyr Gly Tyr Leu
305                 310                 315                 320

Ser Arg Glu Tyr Ile Tyr Cys Leu Tyr Trp Ser Thr Leu Thr Leu Thr
                325                 330                 335

Thr Ile Gly Glu Thr Pro Pro Val Lys Asp Glu Tyr Leu Phe
        340                 345                 350

Val Ile Phe Asp Phe Leu Ile Gly Val Leu Ile Phe Ala Thr Ile Val
        355                 360                 365

Gly Asn Val Gly Ser Met Ile Ser Asn Met Asn Ala Thr Arg Ala Glu
    370                 375                 380

Phe Gln Ala Lys Ile Asp Ala Val Lys His Tyr Met Gln Phe Arg Lys
385                 390                 395                 400

Val Ser Lys Glu Met Glu Ala Lys Val Ile Arg Trp Phe Asp Tyr Leu
                405                 410                 415

Trp Thr Asn Lys Lys Ser Val Asp Glu Arg Glu Val Leu Lys Asn Leu
                420                 425                 430

Pro Ala Lys Leu Arg Ala Glu Ile Ala Ile Asn Val His Leu Ser Thr
        435                 440                 445

Leu Lys Lys Val Arg Ile Phe Gln Asp Cys Glu Ala Gly Leu Leu Val
    450                 455                 460

Glu Leu Val Leu Lys Leu Arg Pro Gln Val Phe Ser Pro Gly Asp Tyr
465                 470                 475                 480

Ile Cys Arg Lys Gly Asp Ile Gly Lys Glu Met Tyr Ile Ile Lys Glu
                485                 490                 495

Gly Lys Leu Ala Val Val Ala Asp Asp Gly Val Thr Gln Tyr Ala Leu
            500                 505                 510

Leu Ser Ala Gly Ser Cys Phe Gly Glu Ile Ser Ile Leu Asn Ile Lys
        515                 520                 525

Gly Ser Lys Met Gly Asn Arg Arg Met Ala Asn Ile Arg Ser Leu Gly
    530                 535                 540

Tyr Ser Asp Leu Phe Cys Leu Ser Lys Asp Asp Leu Met Glu Ala Val
545                 550                 555                 560

Thr Glu Tyr Pro Asp Ala Lys Arg Val Leu Glu Glu Arg Gly Arg Glu
                565                 570                 575
```

-continued

```
Ile Leu Met Lys Glu Gly Leu Leu Asp Glu Asn Glu Val Ala Ala Ser
            580                 585                 590
Met Glu Val Asp Val Gln Glu Lys Leu Glu Gln Leu Glu Thr Asn Met
            595                 600                 605
Asp Thr Leu Tyr Thr Arg Phe Ala Arg Leu Leu Ala Glu Tyr Thr Gly
            610                 615                 620
Ala Gln Gln Lys Leu Lys Gln Arg Ile Thr Val Leu Glu Thr Lys Met
625                 630                 635                 640
Lys Gln Asn Asn Glu Asp Asp Ser Leu Ser Asp Gly Met Asn Ser Pro
                645                 650                 655
Glu Pro Pro Ala Glu Lys Pro
            660

<210> SEQ ID NO 5
<211> LENGTH: 1989
<212> TYPE: DNA
<213> ORGANISM: Bovine
<220> FEATURE:
<221> NAME/KEY: CDS
<222> LOCATION: (1)..(1989)
<223> OTHER INFORMATION: Nucleic Acid sequence of genetically modified
      bovine T537V- 3-subunit of cyclic nucleotide gated-ion channels

<400> SEQUENCE: 5 atg aca gaa aaa gcc aat ggc gtg aag agc tcc cca gcc aat aac cac      48
Met Thr Glu Lys Ala Asn Gly Val Lys Ser Ser Pro Ala Asn Asn His
  1               5                  10                  15 aac cac cat gcc cct cct gcc atc aag gcc agt ggc aaa gat gac cac      96
Asn His His Ala Pro Pro Ala Ile Lys Ala Ser Gly Lys Asp Asp His
                 20                  25                  30 agg gcc agc agc cgg cca cag tct gct gct gct gat gac acc tcc tca     144
Arg Ala Ser Ser Arg Pro Gln Ser Ala Ala Ala Asp Asp Thr Ser Ser
             35                  40                  45 gag cta cag caa ctg gca gag atg gat gcc ccc cag cag agg agg ggt     192
Glu Leu Gln Gln Leu Ala Glu Met Asp Ala Pro Gln Gln Arg Arg Gly
         50                  55                  60 ggc ttc cgc agg att gcc cgc ctg gtg ggg gtc ctc aga gag tgg gct     240
Gly Phe Arg Arg Ile Ala Arg Leu Val Gly Val Leu Arg Glu Trp Ala
 65                  70                  75                  80 tac agg aac ttc cgt gag gag gag cct aga cct gac tca ttc ctt gag     288
Tyr Arg Asn Phe Arg Glu Glu Glu Pro Arg Pro Asp Ser Phe Leu Glu
                 85                  90                  95 cgt ttc cgg ggg cct gag ctc cac acc gtg aca aca caa caa gga gac     336
Arg Phe Arg Gly Pro Glu Leu His Thr Val Thr Thr Gln Gln Gly Asp
                100                 105                 110 ggc aaa ggc gac aag gac ggc gag ggc aag ggc acc aag aag aag ttt     384
Gly Lys Gly Asp Lys Asp Gly Glu Gly Lys Gly Thr Lys Lys Lys Phe
            115                 120                 125 gaa ctc ttt gtc ttg gac cca gcc ggg gac tgg tac tac cgc tgg ctt     432
Glu Leu Phe Val Leu Asp Pro Ala Gly Asp Trp Tyr Tyr Arg Trp Leu
        130                 135                 140 ttt ctc att gcc ttg ccc gtc ctc tac aac tgg tgc cta ttg gtg gcc     480
Phe Leu Ile Ala Leu Pro Val Leu Tyr Asn Trp Cys Leu Leu Val Ala
145                 150                 155                 160 aga gcc tgc ttc agt gac ctg cag aaa ggc tac tac ata gtg tgg ctg     528
Arg Ala Cys Phe Ser Asp Leu Gln Lys Gly Tyr Tyr Ile Val Trp Leu
                165                 170                 175 gtg ctg gat tac gtc tca gat gtg gtc tac atc gca gac ctc ttc atc     576
Val Leu Asp Tyr Val Ser Asp Val Val Tyr Ile Ala Asp Leu Phe Ile
            180                 185                 190
```

-continued

| | |
|---|---|
| cga ctg cgc aca ggt ttc ttg gag cag ggg cta ctg gtg aaa gac acc<br>Arg Leu Arg Thr Gly Phe Leu Glu Gln Gly Leu Leu Val Lys Asp Thr<br>        195                     200                 205 | 624 |
| aag aag ttg cgg gac aac tac atc cac acc atg cag ttt aag ctg gat<br>Lys Lys Leu Arg Asp Asn Tyr Ile His Thr Met Gln Phe Lys Leu Asp<br>    210                     215                 220 | 672 |
| gtg gcc tcc atc atc cct aca gac ctg atc tat ttt gct gtg ggg atc<br>Val Ala Ser Ile Ile Pro Thr Asp Leu Ile Tyr Phe Ala Val Gly Ile<br>225                   230                 235                 240 | 720 |
| cat aac cct gag gtg cgc ttc aac cgc ctg cta cac ttt gcc cgc atg<br>His Asn Pro Glu Val Arg Phe Asn Arg Leu Leu His Phe Ala Arg Met<br>               245                 250                 255 | 768 |
| ttt gag ttc ttt gac cgc act gag aca cgc acc agc tac ccc aac atc<br>Phe Glu Phe Phe Asp Arg Thr Glu Thr Arg Thr Ser Tyr Pro Asn Ile<br>                   260                 265                 270 | 816 |
| ttc cga ata agc aac ctg atc ctc tac atc ttg atc atc att cac tgg<br>Phe Arg Ile Ser Asn Leu Ile Leu Tyr Ile Leu Ile Ile Ile His Trp<br>        275                     280                 285 | 864 |
| aat gcc tgc atc tac tat gcc atc tcc aag tcc atc ggc ttt ggg gta<br>Asn Ala Cys Ile Tyr Tyr Ala Ile Ser Lys Ser Ile Gly Phe Gly Val<br>    290                     295                 300 | 912 |
| gac acc tgg gtt tac ccc aac atc act gac cct gag tat ggc tac ctg<br>Asp Thr Trp Val Tyr Pro Asn Ile Thr Asp Pro Glu Tyr Gly Tyr Leu<br>305                   310                 315                 320 | 960 |
| tct agg gag tac atc tat tgc ctt tac tgg tct aca ctg acc ctc acc<br>Ser Arg Glu Tyr Ile Tyr Cys Leu Tyr Trp Ser Thr Leu Thr Leu Thr<br>               325                 330                 335 | 1008 |
| acc att ggg gag aca cca ccc cct gta aag gat gag gag tac ctg ttt<br>Thr Ile Gly Glu Thr Pro Pro Pro Val Lys Asp Glu Glu Tyr Leu Phe<br>              340                 345                 350 | 1056 |
| gtc atc ttt gac ttc ctg att ggt gtc ctc atc ttt gcc acc atc gtg<br>Val Ile Phe Asp Phe Leu Ile Gly Val Leu Ile Phe Ala Thr Ile Val<br>             355                 360                 365 | 1104 |
| gga aat gtg ggc tcc atg atc tcc aac atg aat gcc acc cgg gct gag<br>Gly Asn Val Gly Ser Met Ile Ser Asn Met Asn Ala Thr Arg Ala Glu<br>370                   375                 380 | 1152 |
| ttc cag gcc aag att gat gct gtc aaa cat tat atg cag ttc cga aag<br>Phe Gln Ala Lys Ile Asp Ala Val Lys His Tyr Met Gln Phe Arg Lys<br>385                   390                 395                 400 | 1200 |
| gtc agc aag gag atg gaa gcc aag gtc att agg tgg ttt gac tac ttg<br>Val Ser Lys Glu Met Glu Ala Lys Val Ile Arg Trp Phe Asp Tyr Leu<br>                   405                 410                 415 | 1248 |
| tgg acc aat aag aag agt gta gat gag cga gaa gtc ctc aaa aac ctg<br>Trp Thr Asn Lys Lys Ser Val Asp Glu Arg Glu Val Leu Lys Asn Leu<br>             420                     425                 430 | 1296 |
| cca gca aag ctc agg gct gag ata gcc atc aac gtc cac ctg tcc aca<br>Pro Ala Lys Leu Arg Ala Glu Ile Ala Ile Asn Val His Leu Ser Thr<br>                   435                 440                 445 | 1344 |
| ctc aag aaa gtg cgc atc ttt cag gac tgt gag gct ggc ctg ctg gtg<br>Leu Lys Lys Val Arg Ile Phe Gln Asp Cys Glu Ala Gly Leu Leu Val<br>    450                     455                 460 | 1392 |
| gaa ctg gta tta aag ctc cgg cct cag gtc ttt agc cct ggg gac tac<br>Glu Leu Val Leu Lys Leu Arg Pro Gln Val Phe Ser Pro Gly Asp Tyr<br>465                   470                 475                 480 | 1440 |
| att tgc cgc aag ggg gat att ggg aag gag atg tac ata atc aag gag<br>Ile Cys Arg Lys Gly Asp Ile Gly Lys Glu Met Tyr Ile Ile Lys Glu<br>               485                 490                 495 | 1488 |
| gga aaa ttg gca gtg gtg gct gat gac ggt gtc act cag tat gcc ctg<br>Gly Lys Leu Ala Val Val Ala Asp Asp Gly Val Thr Gln Tyr Ala Leu<br>              500                 505                 510 | 1536 |

```
ctc tcg gct ggg agt tgc ttt gga gag atc agt atc ctt aat att aag    1584
Leu Ser Ala Gly Ser Cys Phe Gly Glu Ile Ser Ile Leu Asn Ile Lys
        515                 520                 525 ggc agc aaa atg ggc aat cgg cgc gtc gcc aac atc cgc agt ctt ggc    1632
Gly Ser Lys Met Gly Asn Arg Arg Val Ala Asn Ile Arg Ser Leu Gly
530                 535                 540 tac tct gat ctg ttc tgc ttg tcc aag gat gat ctt atg gaa gct gtg    1680
Tyr Ser Asp Leu Phe Cys Leu Ser Lys Asp Asp Leu Met Glu Ala Val
545                 550                 555                 560 act gag tac cct gat gcc aag agg gtc ttg gag gag aga ggc cgg gag    1728
Thr Glu Tyr Pro Asp Ala Lys Arg Val Leu Glu Glu Arg Gly Arg Glu
                565                 570                 575 att ctg atg aag gag ggc ttg ttg gat gag aat gag gtg gca gcc agc    1776
Ile Leu Met Lys Glu Gly Leu Leu Asp Glu Asn Glu Val Ala Ala Ser
        580                 585                 590 atg gag gta gat gtg cag gaa aag cta gaa cag ctg gag acc aac atg    1824
Met Glu Val Asp Val Gln Glu Lys Leu Glu Gln Leu Glu Thr Asn Met
    595                 600                 605 gac acc ttg tac act cgt ttt gcc cgc ctg ctg gcc gag tac acg gga    1872
Asp Thr Leu Tyr Thr Arg Phe Ala Arg Leu Leu Ala Glu Tyr Thr Gly
610                 615                 620 gcc cag cag aag ctc aag cag cgc atc aca gtt ttg gaa acg aag atg    1920
Ala Gln Gln Lys Leu Lys Gln Arg Ile Thr Val Leu Glu Thr Lys Met
625                 630                 635                 640 aag cag aat aat gag gat gac tcc ctg tca gat ggg atg aac agc cca    1968
Lys Gln Asn Asn Glu Asp Asp Ser Leu Ser Asp Gly Met Asn Ser Pro
                645                 650                 655 gag cca cct gcc gag aag cca                                        1989
Glu Pro Pro Ala Glu Lys Pro
                660

<210> SEQ ID NO 6
<211> LENGTH: 663
<212> TYPE: PRT
<213> ORGANISM: Bovine

<400> SEQUENCE: 6

Met Thr Glu Lys Ala Asn Gly Val Lys Ser Ser Pro Ala Asn His
 1               5                  10                  15

Asn His His Ala Pro Pro Ala Ile Lys Ala Ser Gly Lys Asp Asp His
             20                  25                  30

Arg Ala Ser Ser Arg Pro Gln Ser Ala Ala Asp Asp Thr Ser Ser
         35                  40                  45

Glu Leu Gln Gln Leu Ala Glu Met Asp Ala Pro Gln Gln Arg Arg Gly
     50                  55                  60

Gly Phe Arg Arg Ile Ala Arg Leu Val Gly Val Leu Arg Glu Trp Ala
 65                  70                  75                  80

Tyr Arg Asn Phe Arg Glu Glu Pro Arg Pro Asp Ser Phe Leu Glu
                 85                  90                  95

Arg Phe Arg Gly Pro Glu Leu His Thr Val Thr Thr Gln Gln Gly Asp
            100                 105                 110

Gly Lys Gly Asp Lys Asp Gly Glu Gly Lys Gly Thr Lys Lys Lys Phe
        115                 120                 125

Glu Leu Phe Val Leu Asp Pro Ala Gly Asp Trp Tyr Tyr Arg Trp Leu
    130                 135                 140

Phe Leu Ile Ala Leu Pro Val Leu Tyr Asn Trp Cys Leu Leu Val Ala
145                 150                 155                 160

Arg Ala Cys Phe Ser Asp Leu Gln Lys Gly Tyr Tyr Ile Val Trp Leu
                165                 170                 175
```

```
Val Leu Asp Tyr Val Ser Asp Val Tyr Ile Ala Asp Leu Phe Ile
            180                 185                 190

Arg Leu Arg Thr Gly Phe Leu Glu Gln Gly Leu Leu Val Lys Asp Thr
            195                 200                 205

Lys Lys Leu Arg Asp Asn Tyr Ile His Thr Met Gln Phe Lys Leu Asp
            210                 215                 220

Val Ala Ser Ile Ile Pro Thr Asp Leu Ile Tyr Phe Ala Val Gly Ile
225                 230                 235                 240

His Asn Pro Glu Val Arg Phe Asn Arg Leu Leu His Phe Ala Arg Met
            245                 250                 255

Phe Glu Phe Phe Asp Arg Thr Glu Thr Arg Thr Ser Tyr Pro Asn Ile
            260                 265                 270

Phe Arg Ile Ser Asn Leu Ile Leu Tyr Ile Leu Ile Ile His Trp
            275                 280                 285

Asn Ala Cys Ile Tyr Tyr Ala Ile Ser Lys Ser Ile Gly Phe Gly Val
            290                 295                 300

Asp Thr Trp Val Tyr Pro Asn Ile Thr Asp Pro Glu Tyr Gly Tyr Leu
305                 310                 315                 320

Ser Arg Glu Tyr Ile Tyr Cys Leu Tyr Trp Ser Thr Leu Thr Leu Thr
            325                 330                 335

Thr Ile Gly Glu Thr Pro Pro Pro Val Lys Asp Glu Glu Tyr Leu Phe
            340                 345                 350

Val Ile Phe Asp Phe Leu Ile Gly Val Leu Ile Phe Ala Thr Ile Val
            355                 360                 365

Gly Asn Val Gly Ser Met Ile Ser Asn Met Asn Ala Thr Arg Ala Glu
            370                 375                 380

Phe Gln Ala Lys Ile Asp Ala Val Lys His Tyr Met Gln Phe Arg Lys
385                 390                 395                 400

Val Ser Lys Glu Met Glu Ala Lys Val Ile Arg Trp Phe Asp Tyr Leu
            405                 410                 415

Trp Thr Asn Lys Lys Ser Val Asp Glu Arg Glu Val Leu Lys Asn Leu
            420                 425                 430

Pro Ala Lys Leu Arg Ala Glu Ile Ala Ile Asn Val His Leu Ser Thr
            435                 440                 445

Leu Lys Lys Val Arg Ile Phe Gln Asp Cys Glu Ala Gly Leu Leu Val
            450                 455                 460

Glu Leu Val Leu Lys Leu Arg Pro Gln Val Phe Ser Pro Gly Asp Tyr
465                 470                 475                 480

Ile Cys Arg Lys Gly Asp Ile Gly Lys Glu Met Tyr Ile Ile Lys Glu
            485                 490                 495

Gly Lys Leu Ala Val Val Ala Asp Asp Gly Val Thr Gln Tyr Ala Leu
            500                 505                 510

Leu Ser Ala Gly Ser Cys Phe Gly Glu Ile Ser Ile Leu Asn Ile Lys
            515                 520                 525

Gly Ser Lys Met Gly Asn Arg Arg Val Ala Asn Ile Arg Ser Leu Gly
            530                 535                 540

Tyr Ser Asp Leu Phe Cys Leu Ser Lys Asp Asp Leu Met Glu Ala Val
545                 550                 555                 560

Thr Glu Tyr Pro Asp Ala Lys Arg Val Leu Glu Glu Arg Gly Arg Glu
            565                 570                 575

Ile Leu Met Lys Glu Gly Leu Leu Asp Glu Asn Glu Val Ala Ala Ser
            580                 585                 590

Met Glu Val Asp Val Gln Glu Lys Leu Glu Gln Leu Glu Thr Asn Met
```

-continued

```
                    595                 600                 605
Asp Thr Leu Tyr Thr Arg Phe Ala Arg Leu Leu Ala Glu Tyr Thr Gly
        610                 615                 620
Ala Gln Gln Lys Leu Lys Gln Arg Ile Thr Val Leu Glu Thr Lys Met
625                 630                 635                 640
Lys Gln Asn Asn Glu Asp Asp Ser Leu Ser Asp Gly Met Asn Ser Pro
                645                 650                 655
Glu Pro Pro Ala Glu Lys Pro
            660

<210> SEQ ID NO 7
<211> LENGTH: 26
<212> TYPE: DNA
<213> ORGANISM: Artificial Sequence
<220> FEATURE:
<223> OTHER INFORMATION: Mutagenic Primer for preparation of
      T537M- 3-subunit

<400> SEQUENCE: 7
cgacgcatgg cgaacatccg cagtct                                        26

<210> SEQ ID NO 8
<211> LENGTH: 26
<212> TYPE: DNA
<213> ORGANISM: Artificial Sequence
<220> FEATURE:
<223> OTHER INFORMATION: Mutagenic Primer for preparation of
      T537V- 3-subunit

<400> SEQUENCE: 8
cgacgcgtcg cgaacatccg cagtct                                        26

<210> SEQ ID NO 9
<211> LENGTH: 30
<212> TYPE: DNA
<213> ORGANISM: Artificial Sequence
<220> FEATURE:
<223> OTHER INFORMATION: PCR-Primer #1817

<400> SEQUENCE: 9
ttggctgcag ctattatggc ttctcggcag                                    30

<210> SEQ ID NO 10
<211> LENGTH: 27
<212> TYPE: DNA
<213> ORGANISM: Artificial Sequence
<220> FEATURE:
<223> OTHER INFORMATION: flanking Primer #1813

<400> SEQUENCE: 10
gtcggatcct ccacactcaa gaaagtg                                       27

<210> SEQ ID NO 11
<211> LENGTH: 30
<212> TYPE: DNA
<213> ORGANISM: Artificial Sequence
<220> FEATURE:
<223> OTHER INFORMATION: Primer #843 for cloning CRF-Receptors

<400> SEQUENCE: 11
agcgggatcc accatgggac ggcgcccgca                                    30

<210> SEQ ID NO 12
<211> LENGTH: 18
<212> TYPE: DNA
```

```
<213> ORGANISM: Artificial Sequence
<220> FEATURE:
<223> OTHER INFORMATION: Primer #842 for cloning CRF-Receptors

<400> SEQUENCE: 12
ggcctggagc tcacactg                                                    18
```

GENETICALLY MODIFIED CYCLIC-NUCLEOTIDE CONTROLLED ION CHANNELS

CROSS REFERENCE TO RELATED APPLICATION

This application is a continuation of copending application Ser. No. 10/486,316 filed 2 Jul. 2004 issued as U.S. Pat. No. 7,417,117 B2 as the US national phase of PCT application PCT/EP02/008756 filed 6 Aug. 2002 (published 20 Feb. 2003 as WO 2003/014149) with a claim to the priority of German 101 38 876.4 filed 8 Aug. 2001.

FIELD OF THE INVENTION

The present invention relates to genetically modified nucleic acids, preferably DNAs, which code for cyclic nucleotide-gated ion channels (CNG channels) and the corresponding proteins and the use thereof.

BACKGROUND OF THE INVENTION

Chemical substances such as, for example, hormones or neurotransmitters may bind as "primary messengers" (ligands) to the membrane of cells and thereby trigger a large variety of biochemical-physiological reactions inside these cells, which enable the latter to respond to their environment. This process is mediated by a large number of membrane-bound receptors to which ligands can bind specifically and directly. It is at the beginning of different, partly extremely complex transaction cascades. Receptors control and regulate via such cascades the activity of different cellular proteins (effector proteins). These effector proteins for their part can in turn regulate the concentration of intracellular messengers, the "secondary messengers". Only such secondary messengers control a multiplicity of physiological reactions such as, for example, synthesis and release of hormones and neurotransmitters, cell division and cell growth and excitation and excitability of neuronal cells. Particularly important secondary messengers include cyclic adenosine monophosphate (cAMP), cyclic guanosine monophosphate (cGMP) and $Ca^{2+}$ ions.

The intracellular concentration of secondary messengers is usually regulated by signal transduction cascades in which G protein-coupled receptors in the membrane of cells (GPCRs) register an extracellular signal then activate corresponding G proteins which in turn either stimulate or inhibit the activity of the corresponding effector proteins (Morris A. J. and Malbon C. C. (1999) Physiological regulation of G protein-linked signaling. Physiol. Rev., 79, 1373-1430). In addition, other proteins can modulate the activity of each individual component within the framework of a large variety of feedback mechanisms.

Deviations from the physiologically normal concentration of ligands or disruptions in the course of a signal transduction cascade, caused, for example, by the malfunction of a component involved therein, may cause severe diseases. Since GPCRs represent a particularly important interface between the extracellular and intracellular medium of the cell by serving as binding site or site of attack of a very large number of endogenous and exogenous chemical substances and, moreover, controlling in a large variety important physiological processes in virtually any vital organ or tissue, they are of outstanding interest for medical-pharmacological interventions. Particularly important areas of indication in this connection are disorders of the central and peripheral nervous system, of the cardiovascular system and the inner organs.

A therapeutic goal of the pharmaceutical industry is to develop pharmacological active compounds which activate (agonists), inhibit (antagonists) the target proteins or else modulate the activity thereof. This additionally requires detailed functional characterization of the appropriate target proteins. For this purpose, different methods have been developed in recent years, which differ, some of them markedly, with respect to their flexibility, but also to the meaningfulness of the results obtained therewith, and to their robustness and their effectiveness regarding speed, amount of work required and costs.

Now that the complementary DNA of a multiplicity of receptors have been cloned and these receptors can be expressed functionally in cell systems, the studies are carried out mainly on heterologously expressed receptors. The prior art regarding the strategies and methods used and application thereof are described, for example, in articles by Hertzberg R. P. and Pope A. J. (2000) High-throughput screening: new technology for the 21st century. Curr. Opin. Chem. Biol., 4, 445-451, Howard A. D., MacAllister G., Feighner S. D., Liu Q., Nargund R. P., van der Ploeg L. H., and Patchett A. A. (2001) Orphan G-protein-coupled receptors and natural ligand discovery. Trends Pharmacol. Sci., 22, 132-140, Civelli O., Northacker H. P., Saito Y., Wang Z., Lin S. H. and Reinscheid R. K., (2001) Novel neuro-transmitters as natural ligands of orphan G-protein-coupled receptors. Trends Neurosci., 24, 230-237, and also in the references contained therein.

More than 60% of the GPCRs known regulate the intracellular concentration of the secondary messenger cAMP. Different methods exist for studying the effect of chemical substances on such GPCRs and the corresponding effector proteins.

Some of these methods are based on direct, usually radiochemical, measurements of intracellular cAMP concentration. For this purpose, for example, the cells are stimulated, biochemically disrupted after a defined period of time and the change in cAMP concentration is determined. Although these measurement methods are very sensitive, they are usually inherently slow, cost-intensive and time-consuming. It is, moreover, not possible to monitor the change in intracellular cAMP concentration in real time. Important characteristic properties such as speed and course of an activation or inhibition can be determined only by a multiplicity of additional measurements at considerable additional expense. On the other hand, these methods are advantageous in that it is possible to study the effect of active compounds not only on GPCRs but also on the effector proteins which regulate intracellular cAMP concentration.

Another method which may be used for measuring intracellular changes in cAMP or cGMP concentration makes use of the properties of membrane-bound CNG channels. Cyclic nucleotide-gated ion channels (CNG channels) are membrane-bound proteins which have the features and properties described below (Finn J. T., Grunwald M. E. and Yau K. W. (1996) Cyclic nucleotide-gated ion channels: an extended family with diverse functions. Annu. Rev. Physio., 58, 395-426; Richards M. J. and Gordon S. E. (2000) Cooperativity and cooperation in cyclic nucleotide-gated ion channels. Biochemistry, 39, 14003-14011). CNG channels comprise (1) presumably 4 or 5 subunits (α and/or β subunits) which (2) in each case span the membrane six times and (3) possess in each case a binding site for cyclic nucleotides at the carboxy-terminal intracellular end. CNG channels are (4) activated directly and in a manner dose-dependent by cAMP or cGMP, form (5) an aqueous pore in the membrane with a conductivity which is only slightly selective for monovalent cations and are (6) likewise permeable for divalent cations such as $Ca^{2+}$ ions, for example.

"Binding site for cyclic nucleotides" refers to that section in the CNG channel subunits to which the cyclic nucleotides cAMP and cGMP can bind in a dose-dependent manner. The amino acid sequence in this section determines to a considerable extent the sensitivity of a CNG channel for cAMP or cGMP (sensitivity).

"Conductivity" refers to the property of ion channels of enabling in a more or less selective manner ions to flow from the outside of the cell into the cell interior or to flow out of the cell interior to the outside. For this purpose, the ion channels form an opening in the membrane (aqueous pore), through which, depending on the state of activation of these channels, ions can flow in or out, according to the concentration gradient.

It is possible in heterologous expression systems to express functional CNG channels from identical α subunits (homooligomers; Kaupp U. B., Niidome T., Tanabe T., Terada S., Bonigk W., Stuhmer W., Cook N. J., Kanagawa K., Matsuo H., Hirose T., Miyata T. and Numa S. (1989) Primary structure and functional expression from complementary DNA of the rod photoreceptor cyclic GMP-gated channel. Nature, 342, 762-766), from different a subunits (heterooligomers; Bradley J., Li J., Davidson N., Lester H. A. and Zinn K. (1994) Heteromeric olfactory cyclic nucleotide-gated channels: a subunit that confers increased sensitivity to cAMP, Proc. Natl. Acad. Sci. USA, 91, 8890-8894; Liman E. R. and Buck L. B. (1994) A second subunit of the olfactory cyclic nucleotide-gated channel confers high sensitivity to cAMP. Neuron 13, 611-621), and as heterooligomers from α and β subunits (Chan T. Y., Peng Y. W., Dhallan R. S., Ahamed B., Reed R. R. and Yau K. W. (1993) A new subunit of the cyclic nucleotide-gated cation channel in retinal rods. Nature, 362, 764-767). The β subunits alone cannot form functional channels but have exclusively modulatory functions in heterooligomeric CNG channels (Chen T. Y., Peng Y. W., Dhallan R. S., Ahamed B., Reed R. R. and Yau K. W. (1993) A new subunit of the cyclic nucleotide-gated cation channel in retinal rods. Nature, 362, 764-767). When cAMP or cGMP binds to CNG channels, these channels open in a dose-dependent manner and ions flow into the cell. Activation of the CNG channels results under physiological conditions in an increased $Ca^{2+}$ conductivity of these channels and thus causes the increase in intracellular $Ca^{2+}$ concentration. A change in concentration of this kind can be measured using optical $Ca^{2+}$ measurement methods. Thus, these ion channels could in principle be used as cellular cAMP sensor for studying and characterizing any receptors and intracellular proteins which regulate intracellular cAMP concentration. This method is very rapid, effective and inexpensive in comparison with direct cAMP measurements. It allows a high throughput of tests per day and makes real-time measurements possible. This method is therefore in principle particularly suitable for pharmacological drug screening.

The documents U.S. Pat. No. 6,001,581 and WO 98/58074 and Gotzes F. (1995) Dissertation. ISSN 0944-2952 describe the use as cAMP sensor of CNG channels comprising the α3 subunits from the epithelium of the nose. However, such CNG channels have several decisive disadvantages when used as cellular cAMP sensors in pharmaceutical drug screening. As little as 2 μM cGMP activates these CNG channels but only 80 μM cAMP produces half-maximum activation thereof (Dhallan R. S., Yau K. W., Schrader K. A. and Reed R. R. (1990) Primary structure and functional expression of a cyclic nucleotide-activated channel from olfactory neurons. Nature, 347, 184-187; Ludwig J., Margalit T., Eismann E., Lancet D. and Kaupp U. B. (1990) Primary structure of cAMP-gated channel from bovine olfactory epithelium. FEBS Lett. 270, 24-29). However, since intracellular cAMP concentration usually changes only by a few μM, such CNG channels are only poorly suitable as cAMP sensors, although they are suitable as cGMP sensors in principle. Moreover, even small fluctuations in intracellular cGMP concentration can interfere with the cAMP concentration measurements.

In contrast, half-maximum activation ($K_{1/2}$ value) of heterooligomeric CNG channels composed of α3, α4 and β1b subunits is already obtained at a cAMP concentration of about 4 μM, while $K_{1/2}$ for cGMP changes only insignificantly in comparison with the homooligomeric channels (Bonigk W., Bradley J., Muller F., Sesti F., Boekhoff I., Ronnett G. V., Kaupp U. B and Frings S., (1999) The native rat olfactory cyclic nucleotide-gated channel is composed of three distinct subunits. J. Neurosci., 19, 5332-5347. CNG channels of this kind have in principle excellent suitability as cellular cAMP sensors. Disadvantageously, however, expression of such channels in heterologous cell systems requires a lot of work and time. Moreover, small fluctuations in intracellular cGMP concentration may interfere with the cAMP sensor function.

However, it is also possible to use molecular-biological methods for preparing CNG channels which comprise only α subunits but are nevertheless highly sensitive to cAMP: in 1991, a genetically modified α3 subunit of the bovine CNG channel was described, in which subunit threonine at position 537 had been replaced with a serine (T537S) (Altenhofen W., Ludwig J., Eismann E., Kraus W., Bonigk W. and Kaupp U. B. (1991) Control of ligand specificity in cyclic nucleotide-gated channel from rod photoreceptors and olfactory epithelium. Proc. Natl. Acad. Sci. USA, 88, 9868-9872). This subunit forms CNG channels whose half-maximum activation is produced by 14 μM cAMP. Threonine T537 is located in the sequence section of the α3 subunit, which is involved to a considerable extent in binding of the cyclic nucleotides. Evidently, the amino acid in this position is particularly important for the sensitivity of the CNG channels (Altenhofen W., Ludwig J., Eismann E., Kraus W., Bonigk W. and Kaupp U. B. (1991) Control of ligand specificity in cyclic nucleotide-gated channel from rod photoreceptors and olfactory epithelium. Proc. Natl. Acad. Sci. USA, 88, 9868-9872). However, this mutation, T537S, also increases the sensitivity of the channels to cGMP ($K_{1/2}$=0.7 μM). Such channels (T537S mutants) can be expressed heterologously with low expenditure, but they are, as cAMP sensor, even more susceptible to interference from small fluctuations in intracellular cGMP concentration than the heterooligomeric channels. Moreover, the sensitivity to cAMP is still not high enough in order to reliably register also small fluctuations in intracellular cAMP concentration.

Furthermore, mutations in the α3 subunit of the CNG channel are known which increase sensitivity to cAMP and additionally reduce sensitivity to cGMP. (Rich T. C., Tse T. E., Rohan D. G., Schaack J. and Karpen J. W. (2001) In vivo assessment of local phosphodiesterase activity using tailored cyclic nucleotide-gated channels as cAMP sensors. J. Gen. Physiol., 118; 63-78). 1.2 μM cAMP but only 12 μM cGMP produce half-maximum activation of CNG channels composed of the rat α3 subunit in which cysteine in position 460 (C460) has been replaced with tryptophan (W) and, in addition, glutamate in position 583 (E583) has been replaced with methionine (M) (C460W/E583M mutant).

It was the object of the invention to develop CNG channels as cAMP sensors whose sensitivity to cAMP or cGMP is similar to that of the C460W/E583M mutant but which are genetically modified only in one position. Such CNG channels may be used in simple and rapid cellular measuring systems efficiently and universally for pharmaceutical drug screening but also for characterizing pharmacological or potentially pharmacological target proteins.

This object is achieved by CNG channels composed of α3 subunits which have been modified in the position corresponding to threonine T537 in the bovine α3 subunit so as to have higher sensitivity to cAMP and/or higher selectivity for cAMP compared to cGMP in comparison with the wild type according to SEQ ID NO 1 and 2.

These ion channels have a sensitivity to cAMP and cGMP similar to that of the C460W/E583M mutant.

The invention moreover relates to a method for preparing these CNG channels. The invention also relates to expression vectors comprising the nucleic acids for the modified CNG channels. The invention likewise relates to cell lines which are transformed with the described expression vectors and which can express the CNG channels. Particular preference is given to cell lines capable of coexpressing heterologously either GPCRs, adenylate cyclases, phosphodiesterases or other proteins which regulate intracellular cAMP concentration together with a modified CNG channel.

The invention further relates to a method for preparing these cell lines, which comprises carrying out a transformation by means of expression vectors. According to the invention, the genes for the proteins are preferably cloned into the expression vector, followed by transformation of the cell lines.

According to the invention, preference is given to using CNG channels composed of α3 subunits. However, other subunits from bovine or other organisms are also suitable.

In the subunits used according to the invention, preference is given to replacing the amino acid corresponding to threonine at position T537 in the bovine α3 subunit with a different amino acid other than serine. Particular preference is given here to those subunits in which threonine has been replaced with methionine or valine. SEQ ID NO 3 and 4 and, respectively, SEQ ID NO 5 and 6 depict the bovine α3 subunit as an example of subunits modified in this way.

The ion channels of the invention are especially suitable as cellular cAMP sensors for measuring intracellular cAMP concentration. They are also suitable for determining the action of ligands, agonists and antagonists on G protein-coupled receptors (GPCRs) which regulate intracellular cAMP concentration. Moreover, they may be used for determining the action of activators and inhibitors on adenylate cyclases and phosphodiesterases (effector proteins) which regulate intracellular cAMP concentration.

The invention further relates to the use of cellular measuring systems comprising nucleic acids and the corresponding proteins for determining the action of chemical substances which influence the activity of cellular components which regulate intracellular cAMP concentration directly or indirectly.

The cellular measuring systems may be used universally and flexibly as cAMP sensors for pharmaceutical drug screening and drug characterization and for characterization of pharmacologically relevant proteins. The latter include all G protein-coupled receptors, adenylate cyclases, phosphodiesterases and any other proteins involved in cAMP signal pathways.

Cellular cAMP sensors which may be prepared and used instead of the T537M mutant or the C460W/E583M mutant however, are in principle also other genetically modified CNG channels which have (i) a similarly high or higher sensitivity to cAMP,
(ii) a similarly high or higher sensitivity to cAMP or else
(iii) a similarly high or higher sensitivity to and, in addition, a similarly high or higher selectivity for cAMP.

CNG channels of this kind may have (1) α3 subunits of other organisms, (2) other CNG-channel subunits from bovine or other organisms, and (3) a homooligomeric or heterooligomeric composition of these subunits. These subunits may (4) be genetically modified in each case at the position corresponding to position T537 in the α3 subunit of the bovine CNG channel. The threonine in this position may have been replaced with a methionine or a valine or else with another amino acid (with the exception of serine). Such subunits may have (5) further genetic modifications at other positions. These CNG channels may further (6) comprise chimeric subunits which have been genetically modified in the same way at this position.

"Genetically modified at the position corresponding to position T537 in the α3 subunit of the bovine CNG channel" means the following: the different subunits of CNG channels (e.g. α1, α2, α3 and α4) or identical subunits of CNG channels of different organisms, such as, for example, the bovine and rat α3 subunits, have sequences which are highly similar to one another. Nevertheless, the position of the structurally and functionally important sections in the amino acid sequence of these subunits usually differs slightly. The skilled worker, however, is able to identify the sequence sections and amino acids corresponding to one another by comparing the sequences. Threonine T537 in the binding site for cyclic nucleotides in the bovine α3 subunit, for example, corresponds to threonine T539 in the rat α3 subunit or to threonine T560 in the bovine α1 subunit.

"Further genetic modifications" means that, in addition to a modifications of the invention, an amino acid has been replaced with a different one in at least one other position or an amino acid has been deleted from or added to at least one other position.

"Chimeric subunits" means those CNG-channel subunits which are composed of at least two different subunit moieties, i.e., for example, a subunit composed of the amino-terminal moiety of the α1 subunit and the carboxy-terminal moiety of the α3 subunit. Such chimeras can be readily prepared by a skilled worker using molecular-biological methods and are often utilized in order to combine particular properties of one protein with the properties of another protein or to transfer particular properties to another protein or else to alter particular properties in comparison with the wild-type proteins. Chimeras of different CNG-channel subunits have already been described (Seifert R., Eismann E., Ludwig J., Baumann A., and Kaupp, U. B. (1999) Molecular determinants of a $Ca^{2+}$-binding site in the pore of cyclic nucleotide-gated channels: S5/S6 segments control affinity of intrapore glutamates. EMBO J., 18, 119-130).

Six genes for subunits of CNG channels are known in vertebrates (α1-α4, β1, β2). Additionally, there exist different isoforms of these subunits (Sautter A., Zonh X., Hofmann F., and Biel M. (1998) An isoform of the rod photoreceptor cyclic nucleotide-gated channel beta subunit expressed in olfactory. neurons. Proc. Natl. Acad. Sci. USA, 95, 4696-4701; Bonigk W., Bradley J., Muller F., Sesti F., Boekhoff I., Ronnett G. V., Kaupp U. B., and Frings S. (1999) The native rat olfactory cyclic nucleotide-gated channel is composed of three distinct subunits. J. Neurosci., 19, 5332-5347). The α1 subunit (Kaupp U. B., Niidome T., Tanabe T., Terada S., Bonigk W., Stuhmer W., Cook N. J., J., Kangawa K., Matsuo H., Hirose T., Miyata T., and Numa S. (1989) Primary structure and functional expression from complementary DNA of the rod photoreceptor cyclic GMP-gated channel. Nature, 342, 762-766) and the β1 subunit (Chen T. Y., Peng Y. W., Dhallam R. S., Ahamed B., Reed R. R. and Yau K. W. (1993) A new subunit of the cyclic nucleotide-gated cation channel in retinal rods. Nature, 362, 764-767; Korschen H. G., Illing M., Seifert R., Sesti F., Williams A., Gotzes S., Colville C., Muller F., Dose A., Godd M., Molday L., Kaupp U. Be., and Molday R. S. (1995) A 240 kDa protein represents the complete beta subunit of the cyclic nucleotide-gated cation channel from rod photoreceptor. Neuron, 15, 627-636) were first discovered in retinal rods, the α2 subunit (Bonigk W., Altenhofen W., Muller F., Dose A., Illing M., Molday R. S., and Kaupp U. B. (1993) Rod and cone photoreceptor cells express distinct genes for cGMP-gated channels. Neuron, 10, 865-877) and the β2 subunit (Gerstner A., Zong X., Hofmann F., and Biel M. (2000) Molecular cloning and functional characterization of a new modulatory cyclic nucleotide-gated channel subunit from mouse retina. J. Neurosci., 20, 1324-1332) in retinal cones, and the α3 subunit (Dhallan R. S., Yau K. W., Schrader K. A., and Reed R. R. (1990) Primary structure and functional expression of a cyclic nucleotide-activated channel from olfactory neurons. Nature, 347, 184-187; Ludwig J., Margalit T., Eismann E., Lancet D., and Kaupp U. B. (1990) Primary structure of cAMP-gated channel from bovine olfactory epithelium. FEBS Lett., 270, 24-29) and the α4 subunit (Bradley J., Li J., Davidson N., Lester H. A., and Zinn K. (1994) Heteromeric olfactory cyclic nucleotide-gated channels: a subunit that confers increased sensitivity to cAMP. Proc. Natl. Acad. Sci. USA, 91, 8890-8894; Liman E. R. and Buck L. B. (1994) A second subunit of the olfactory cyclic nucleotide-gated channel confers high sensitivity to cAMP. Neuron, 13, 611-621) in olfactory cells of the nose.

In addition, CNG channels composed of these subunits were found in numerous other neuronal and non-neuronal cells and tissues (Richards M. J. and Gordon S. E. (2000) Cooperativity and cooperation in cyclic nucleotide-gated ion channels. Biochemistry, 39, 14003-14011). Moreover, CNG channels were found not only in vertebrates but also in non-vertebrates such as, for example, in *Drosophila melanogaster* (Baumann A., Frings S., Godde M., Seifert R., and Kaupp U. B. (1994) Primary structure and functional expression of a *Drosophila* cyclic nucleotide-gated channel present in eyes and antennae. EMBO J., 13, 5040-5050) and plants (Leng Q., Mercier R. W., Yao W., and Berkowitz G. A. (1999) Cloning and first functional characterization of a plant cyclic nucleotide-gated cation channel. Plant Physiol., 121, 753-761). In principle, these and all other subunits of CNG channels can be modified according to the invention.

The genetically modified CNG channels may be used in cellular test systems as cAMP sensor for pharmacological studies, (i) in order to study the action of ligands, agonists and antagonists on membrane-bound G protein-coupled receptors (GPCRs) which regulate intracellular cAMP concentration, (ii) in order to study the action of activators and inhibitors on effector proteins (enzymes) which synthesize or hydrolyze cAMP, (iii) in order to study the action of activators and inhibitors on other proteins which likewise intervene in the cAMP signal transduction cascade in a regulating manner, but also (iv) in order to study the properties of GPCRs, effector proteins or other proteins involved in cAMP signal transduction cascades.

The proteins referred to as "membrane-bound G protein-coupled receptors" (GPCRs) according to the invention belong to the phylogenetically most varied, extremely extensive family of membrane-bound receptors (overview article: Morris A. J. and Malbon C. C. (1999) Physiological regulation of G protein-linked signaling. Physio. Rev., 79, 1373-1430): The family of GPCRs probably comprises distinctly more than 1,000 different members which can be classified on the basis of their sequence similarity (Probst W. C., Snyder L. A., Schuster D. I., Brosius J., and Sealfon S. C. (1992) Sequence alignment of the G-protein coupled receptor superfamily. DNA Cell Biol., 11, 1-20) or based on the chemical nature of their natural ligands. A compilation and classification of the GPCRs known up to now can be found, for example, in the "GPCRDB" database (Horn F., Weare J., Beukers M. W., Horsch S., Bairoch A., Chen W., Edvardsen O., Campagne F., and Vriend G. (1998) GPCRDB: an information system for G protein-coupled receptors. Nucleic Acids Res., 26, 275-279). Some of the representatives of the individual classes are listed below in the form of an overview. Class A ("rhodopsin-like") includes rhodopsin itself and different sequence-related receptors which are classified on the basis of their natural ligands: these include receptors for (1) biogenic amines such as, for example, the muscarinic acetylcholine receptors, adrenergic receptors, dopamine receptors, histamine receptors, serotonin receptors, octapamine receptors, for (2) peptides, such as, for example, the angiotensin receptors, chemokine receptors, endotheline receptors, neuropeptide receptors, for (3) hormone proteins, such as, for example, FSH receptors, for (4) odorants, for (5) prostanoids, such as, for example, prostaglandin receptors, or for (6) nucleotides, such as, for example, adenosine receptors. Class B ("secretin-like") includes the secretin receptors themselves and, for example, receptors for calcitonin, glucagon, diuretic hormones or CRF (corticotropin-releasing factor). Class C ("metabotropic glutamate/pheromones") includes the metabotropic receptors themselves and also GABA-B receptors and others. Further classes comprise receptors from plants, fungi, insects, bacteria. All classes contain receptors whose function is not yet known or whose natural ligand is not yet known (orphan receptors). The natural ligands of each of about 200 different GPCR types are currently known and about a further 100 GPCR types are orphan GPCRs. 700 or more GPCRs are presumably activated by odorants or tastants. It is possible in principle for all GPCRs regulating intracellular cAMP concentration to be coexpressed with the inventive genetically modified CNG channels as cAMP sensor in heterologous expression systems and for the action of ligands, agonists and antagonists to be studied pharmacologically.

It is also possible to study GPCRs which normally do not regulate intracellular cAMP concentration via stimulatory or inhibitory G proteins. GPCRs of this kind may be altered by genetic modification in such a way that they couple to the cAMP signal pathway. This genetic modification may be carried out, for example, by preparing chimeric GPCRs (Liu J., Conklin B. R., Blin N., Yun J. and Wess J. (1995) Identification of a receptor-G-protein contact site critical for signaling specificity and G protein aviation. Proc. Natl. Acad. Sci. USA, 92, 11642-11646).

"Agonists" and "ligands" refer to substances which activate GCRP.

In contrast, "antagonists" refer to substances which, although being able to bind to GPCRs, cannot activate them. Antagonists inhibit the action of ligands or agonists in a dose-dependent manner.

"Effector proteins" which regulate intracellular cAMP concentration directly include adenylate cyclases and phosphodiesterases.

"Adenylate cyclases" whose activity is controlled in a GPCR-mediated manner are large, membrane-bound enzymes which catalyze the formation of cAMP from $Mg^{2+}$ adenosine triphosphate and which are present in most cells, tissues and organs of the human body (Tang W. J. and Hurley J. H. (1998) Catalytic mechanism and regulation of mammalian adenylyl cyclases. Mol. Pharmacol., 54, 231-240). Nine different classes of these adenylate cyclases are known altogether. Adenylate cyclases of this kind are also endogenously expressed in the cellular test systems of the invention and can be activated by heterologously expressed GPCRs and therefore play a decisive part in the functioning of the test system. Another class comprises soluble adenylate cyclases whose activity is presumably not regulated in a GPCR-mediated manner (Buck J., Sinclair M. L., Schapal L., Cann M. J., and Levin L. R. (2000) Cytosolic adenylyl cyclase defines a unique signaling molecule in mammals. Proc. Natl. Acad. Sci. USA, 96, 79-84). It is possible in principle to coexpress all adenylate cyclases with the inventive genetically modified CNG channels as cAMP sensor in heterologous expression systems and to study pharmacologically the action of inhibitors and activators.

"Phosphodiesterases" (PDEs) are enzymes inside the cell which hydrolyze cAMP and cGMP to give adenosine monophosphate (AMP) and guanosine monophosphate (GMP), respectively (Francis S. H., Turko I. V., and Corbin J. D. (2000) Cyclic nucleotide phosphodiesterases: relating structure and function. Prog. Nucleic Acid Res. Mol. Biol., 65, 1-52). Eleven different types of PDEs are known altogether. Some of these PDEs specifically hydrolyze cGMP, others in turn hydrolyze cAMP, and others again hydrolyze both cAMP and cGMP. Like GPCRs and adenylate cyclases, the PDEs are expressed in most cells, tissues and organs of the human body. In contrast to adenylate cyclases, however, only PDE6 which is specific for photoreceptors is activated in a GPCR-mediated manner. The activity of the other PDEs is instead regulated by different other mechanisms. It is possible in principle to coexpress all PDEs which hydrolyze cAMP with the inventive genetically modified CNG channels as cAMP sensor in heterologous expression systems and to study pharmacologically the action of inhibitors and activators.

"Activators" refers to substances which interact directly with adenylate cyclases or PDEs and thereby increase the enzymatic activity thereof.

"Inhibitors", in contrast, refer to substances which likewise interact directly with adenylate cyclases or PDEs but which reduce the activity thereof.

It is possible in principle for all proteins which regulate intracellular cAMP concentration to be coexpressed with the inventive genetically modified CNG channels as cAMP sensor in heterologous expression systems and to be studied pharmacologically.

The proteins to be studied may be expressed in heterologous systems either transiently or, preferably, stably.

"Transient expression" means that the heterologously expressed protein is expressed by the cells of the expression system only for a defined period of time.

"Stable expression" means that the introduced gene is stably integrated into the genome of the cells of the heterologous expression system. The new cell line produced in this way expresses the corresponding protein in each subsequent cell generation.

For expression, the cDNA coding for the protein to be studied is cloned into an expression vector and transformed into the cells of a suitable expression system.

"Expression vectors" refer to any vectors which can be used for introducing ("transforming") cDNAs into the appropriate cell lines and functionally expressing there the corresponding proteins ("heterologous expression"). Preferably, the transformation may be carried out using the pcDNA vectors (Invitrogen).

Suitable "heterologous expression systems" are in principle all eukaryotic cells such as, for example, yeast, *Aspergillus*, insect, vertebrate and in particular mammalian cells. Examples of suitable cell lines are CHO (Chinese hamster ovary) cells, for example the K1 line (ATCC CCL 61), including the Pro 5 variant (ATCC CRL 1781), COS cells (African green monkey), for example the CV-1 ceu line (ATCC CCL 70), including the COS-1 variant (ATCC CRL 1650) and the COS-7 variant (ATCC 1651), BHK (baby hamster kidney) cells, for example the line BHK-21 (ATCC CCL 10), MRC-5 (ATCC CCL 171), murine L cells, murine NIH/3T3 cells (ATCC CRL 1658), murine C127 cells (ATCC CRL-1616), human carcinoma cells such as, for example, the HeLa line (ATCC CCL 2), neuroblastoma cells of the lines IMR-32 (ATCC CCL 127), neuro-2A cells (ATCC CLL 131), SK-N-MC cells (ATCC HTB 10) and SK-N-SH cells (ATCC HTB 11), PC12 cells (ATCC CRL 1721), and Sf9 cells (*Spodoptera frugiperda*) (ATCC CRL 1711). Preference is given to using HEK 293 (human embryonic kidney) cells (ATCC CRL 1573), including the SF variant (ATCC 1573.1). Particular preference is given to the cell line prepared according to the invention, DSM ACC 2516.

The action of test substances on the protein to be studied can be measured using a fluorescence-optical measurement method.

The protein to be studied is heterologously expressed together with cAMP sensor of the invention in a cellular test system and activated or inhibited by ligands, agonists, antagonists, activators or inhibitors. The cAMP sensor registers the changes in cAMP concentration and $Ca^{2+}$ ions flow into the cell to a larger or reduced extent.

"Fluorescence-optical measurement methods" means that the change in intracellular $Ca^{2+}$ concentration is made visible using a fluorescent $Ca^{2+}$ indicator. By now, a multiplicity of different $Ca^{2+}$ indicators are known (Haugland R. P., (1996) Handbook of fluorescent probes and research chemicals. Molecular Probes Inc.). They include, for example, Fluo-3, Calcium Green, Fura-2 and Fluo-4 (Molecular Probes), the latter being preferred according to the invention. Since indicators of this kind are usually water-soluble and therefore cannot pass the hydrophobic lipid membrane of cells, the indicators are instead applied in the form of an acetoxy methyl ester compound (Tsien R. Y. (1981) A non-disruptive technique for loading calcium buffers and indicators into cell. Nature, 290, 527-528). These compounds, in contrast, are hydrophobic and are taken up by the cells. Inside the cell, the ester bond is cleaved by endogenous, intracellular esterases and the indicator is again present in its water-soluble form in which it remains in the cell interior where it accumulates and can thus be used as intracellular $Ca^{2+}$ indicator. This indicator, when excited with light of a suitable wavelength, then shows fluorescence which depend on the intracellular $Ca^{2+}$ concentration. The degree (amplitude) of fluorescence and the time course (kinetics) correlate with the degree and the time course of activation of the protein studied and can be monitored in real time using fluorescence detectors with a very good signal-to-noise ratio and plotted using a suitable software.

Likewise, the aequorin protein complex which consists of apoaequorin and the chromophoric cofactor coelenterazine or comparable complexes may be used as $Ca^{2+}$ indicators for measuring intracellular $Ca^{2+}$ concentration (Brini M., Pinton P., Pozzan T. and Rizzuto R. (1999) Targeted recombinant aequorins: tools for monitoring (Ca$^{2+}$) in the different compartments of a living cell. Micrsc. Res. Tech., 46, 380-389). For this purpose, apoaequorin must be heterologously expressed together with the cAMP sensor of the invention and the protein to be studied in the cellular test system. Prior to the measurements, the cells must be incubated with coelenterazine so that apoaequorin and coelenterazine can assemble to give the active aequorin complex. When the intracellular Ca$^{2+}$ concentration increases, coelenterazine is oxidized to coelenteramide. In this process, $CO_2$ is formed and luminescence is emitted. Disadvantageously, this process is irreversible. This luminescence may be registered using a suitable optical detector (luminescence-optical measurement method). Although this optical measurement method has a similar sensitivity to the fluorescence-optical measurement method, it is however less suitable for measurements in which the course of the reaction is followed in real time.

Fluorescence- or luminescence-optical measurements using a test system of the invention may be carried out in cuvette measuring devices, in Ca$^{2+}$ imaging microscopes or in fluorescence or luminescence readers.

According to the invention, preference is given to carrying out the measurements in wells of plastic containers (multi-well plates) in fluorescence readers. The cells may be introduced in suspension or else, preferably, attached to the bottom of these wells. Multiwell plates having a different number of wells may be used, such as, for example, multiwell plates having 96, 384, 1536 or more wells. These multiwell plates make it possible to carry out a multiplicity of identical or different measurements in a single plate.

"Fluorescence reader" or "luminescence reader" are very sensitive optical measuring devices which can be used to measure fluorescence or luminescence in multiwell plates. It is possible to study in such devices the action of ligands, agonists, antagonists, activators or inhibitors very rapidly and with a high throughput.

According to the invention, it is possible to study the properties of GPCRs, effector proteins or other proteins involved in cAMP signal transduction cascades quantitatively using fluorescence- or luminescence-optical measurements.

However, it is also possible in principle, according to the invention, to carry out measurements with a high throughput of tests per day. The search for new pharmacological active compounds is thus possible. It is possible here to test up to 100,000 substances per day (high throughput screening, HTS screening) or more than 100,000 substances per day (Ultra-HTS screening, UHTS screening).

Using a FLIPR384 fluorescence reader (Molecular Devices), for example, it is possible to carry out up to 384 independent measurements simultaneously and to monitor fluorescence in real time.

The invention is described in more detail below on the basis of the exemplary embodiments and the attached figures:

EXAMPLES 1-4

Genetically modified, homooligomeric bovine α3 CNG channels were prepared, whose sequence has, in place of threonine T537 of the wild-type channel, a methionine (T537M) or valine (T537V).

For this purpose, the nucleic acid coding for the α3 subunit of the bovine CNG channel (SEQ ID NO 1) was altered in position 537 by site-specific mutagenesis using molecular-biological methods ("genetically modified") so that a nucleic acid coding for the T537M mutant (SEQ ID NO 3) and another one coding for the T537V mutant (SEQ ID NO 5) were generated (see Methods).

The SEQ ID NO 2, 4 and 6 depict the amino acid sequences of the wild-type channel, the T537M mutant and the T537V mutant, respectively.

The sensitivity and selectivity of the T537M mutant and of the T537V mutant for cAMP and cGMP were determined by electrophysiological methods (see Methods) and compared with the properties of the wild-type channel. For this purpose, the corresponding nucleic acids were cloned into the expression vector pcDNA3.1 (Invitrogen) (see Methods). The expression constructs were then used to transform the cells of the human embryonic kidney cell line 293 (HEK293 cells) and the corresponding proteins were functionally expressed therein either transiently or stably (see Methods). The results of the studies are depicted in FIGS. 1-4.

BRIEF DESCRIPTION OF THE DRAWING

FIGS. 1A, 2A, 3A and 4A are a series of graphs plotting the current-voltage relationship in the presence of different concentrations of cAMP (FIG. 1A, FIG. 3A) and cGMP (FIG. 2A, FIG. 4A) for the heterologously expressed genetically modified CNG channels.

FIGS. 1B, 2B, 3B and 4B are a series of graphs plotting the dose-response relationship for the activation of the heterologously expressed genetically modified CNG channels by cAMP (FIG. 1B, 3B) and by cGMP (FIG. 2B, 4B).

FIGS. 1C, 2C, 3C and 4C are a series of graphs plotting the dose-response relationship for the activation of both the wild-type bovine CNG a3 channel and the mutant bovine CNG a3 channels by cAMP (T537M mutant FIG. 1C and T537V mutant FIG. 3C) and by cGMP (T537M mutant FIG. 2C and T537V mutant FIG. 4C).

FIG. 5A is a graph plotting fluorescence against time showing the dose-dependent activation of the transiently expressed *Drosophila* dopamine receptor by dopamine in cells which stably express the T537M mutant of the a3-CNG channel.

FIG. 5G is a graph plotting the dose-response relationship for the activation of the endogenous adenosine receptor by adenosine in cells which stably express the T537M mutant of the a3-CNG channel.

FIG. 5H is a graph plotting fluorescence against time showing the enormous improvement in the cAMP sensitivity of the modified T537M mutant compared with the T537S mutant and the wild-type a3-CNG channel in cells endogenously expressing an adenosine receptor which is stimulated with adenosine to about half-maximum (open circles) or with 25 μM adenosine to maximum (filled circles).

The FIGS. 1A, 2A, 3A and 4A depict in each case the current-voltage (IV) relationship of the heterologously expressed genetically modified CNG channels in the presence of different concentrations of cAMP (1A, 3A) and cGMP (2A, 4A), respectively. They depict in each case a current-voltage relationship typical for CNG channels in the presence of cAMP and cGMP, respectively, and confirm that the channels are functionally expressed in the HEK293 cells.

FIGS. 1-4 B depict the dependence of the average current on the cAMP concentration and cGMP concentration, respectively, in each case in the form of a dose-response relationship. The results of these measurements were used to calculate the sensitivity of the CNG channels to cAMP and cGMP. The concentration of cAMP and cGMP with $V_m=+100$ mV, at which these channels conduct half of the possible maximum current ($K_{1/2}$ value) is used as measure for the sensitivity of these CNG channels. The lower $K_{1/2}$, the higher the sensitivity of the channel to the corresponding cyclic nucleotide.

FIGS. 1B (T537M mutant) and 3B (T537V mutant) depict in each case the dose-response relationship for cAMP; FIGS. 2B (T537M mutant) and 4B (T537V mutant), on the other hand, indicate in each case the dose-response relationship for cGMP.

Figure 1C:
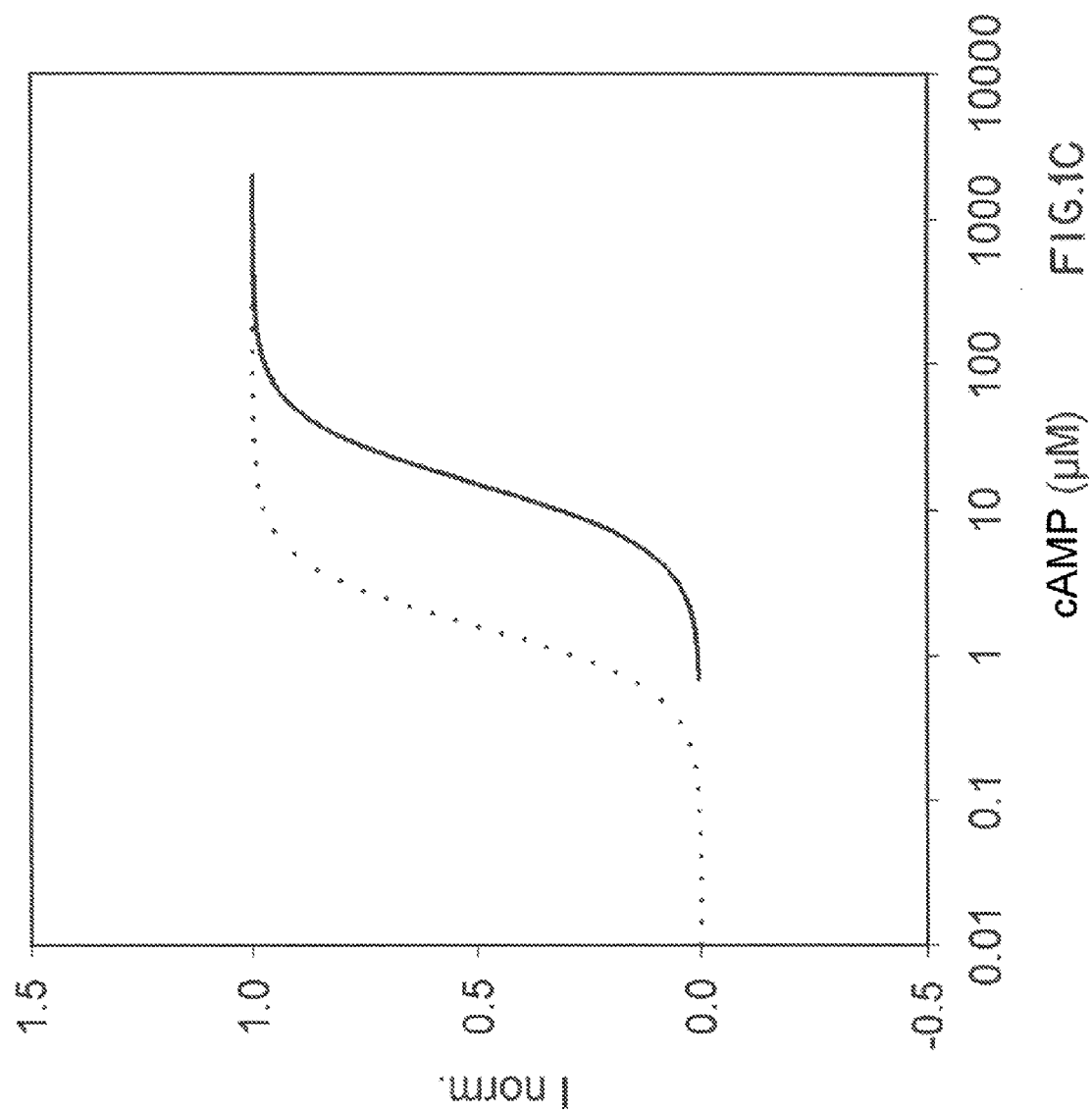

In FIGS. 1C (T537M mutant) and 3C (T537V mutant), in each case the normalized dose-response relationship of the mutants is compared with that of the α3 wild-type channel for cAMP; in FIGS. 2C (T537M mutant) and 4C (T537V mutant), on the other hand, in each case the normalized dose-response relationship is compared with that of the α3 wild-type channel for cGMP.

The table below summarizes the sensitivity properties of the genetically modified CNG channels and the wild-type channel. The $K_{1/2}$ values for cAMP and for cGMP are listed.

|  | $K_{1/2}$ for cAMP | $K_{1/2}$ for cGMP 1. |
| --- | --- | --- |
| 1. Wild Type | 80 μm | 1.6 μm |
| 2. T537S | 14 μm | 0.7 μm |
| 3. T537M | 2.7 μm | 14.9 μm |
| 4. T537V | 34 μm | 241 μm |

Half-maximum activation of the T537M mutant, the T357V mutant and the wild type is produced by 2.7 μm cAMP (FIG. 1C), 34 μm cAMP (FIG. 3C) and 80 μm cAMP (FIGS. 1C, 3C), respectively. The T537M mutant and the T547V mutant are about 30 times and 3 times, respectively, more sensitive to cAMP in comparison with the wild type. In comparison with the T537S mutant, the T537M mutant is about 5 times more sensitive to cAMP, while the T537V mutant is about 2.5 times less sensitive to cAMP than the T537S mutant.

Half-maximum activation of the T537M mutant, the T537V mutant and the wild type is produced by 14.9 μm cGMP (FIG. 2C), 241 μm cGMP (FIG. 4C) and 1.6 μm cGMP (FIGS. 2C, 4C), respectively. Thus, the T537M mutant and the T537V mutant are about 9 times and about 150 times, respectively, less sensitive to cGMP in comparison with the wild type. In comparison with the T537S mutant, the T537M mutant is 21 times less sensitive to cGMP and the T537V mutant is even about 350 times less sensitive to cGMP.

The selectivity of a CNG channel for cAMP or cGMP is obtained by comparing the $K_{1/2}$ values. Example: The T537M mutant has a $K_{1/2}$ of 2.7 μm for cAMP and a $K_{1/2}$ of 14.9 μm for cGMP. This means that half-maximum activation of this mutant is produced by as low as 2.7 μm cAMP but only by 14.9 μm cGMP. According to this, the mutant is markedly more sensitive to cAMP than to cGMP. The quotient (14.9 μm/2.7 μm) indicates the relative selectivity. Thus, the T537M mutant is about 6 times more selective for cAMP. The T537V mutant is likewise about 6 times more selective for cAMP. The T537S mutant, on the other hand, is about 20 times and the wild-type channel even about 50 times more selective for cGMP.

The results of the measurements show the following: CNG-channel mutants whose (1) absolute cAMP sensitivity is very much higher than that of the wild-type channels were generated and identified, and (2) the selectivity for cAMP and cGMP is reversed. The genetic modifications impart an enormous selective sensitivity to cAMP to these CNG channels. In addition, the two genetically modified CNG channels are so insensitive to cGMP that even relatively large changes in intracellular cGMP concentration do not interfere with the cAMP concentration measurement. Specifically, the T537M mutant which is preferred according to the invention is particularly suitable as cellular cAMP sensor. It may be used, for example, in cellular test systems for studying the action of substances which can influence the intracellular cAMP concentration and renders such test systems usable in practice in the first place: a sensor of this kind may then be used to register reliably and with a very good signal-to-noise ratio and monitor in real time even those slight changes in intracellular cAMP concentration as are triggered, for example, by the activation of GPCRs.

Methods

Preparation of Genetically Motivated CNG Channels by Site-Specific Mutagenesis

The cDNA for the α3 subunit of the bovine CNG channel was excised with the aid of suitable restriction endonucleases (Eco RV and Nsi I) from the plasmid pCHOLF102 (Altenhof W., Ludwig J., Eismann E., Kraus W., Bonigk W. and Kaupp U. B. (1991) Control of ligand specificity in cyclic nucleotide-gated channels from rod photoreceptors and olfactory epithelium. Proc. Natl. Acad. Sci. USA, 88, 9868-9872) and cloned into pcDNAlamp (Invitrogen). The plasmid was referred to as pcA-bolf. The cDNA fragment was then cloned via Eco RV and Xba I into pcDNA3 derivatives. The plasmid was referred to as pc3-bolf. The genetically modified α3 subunit of the CNG channel was prepared by means of site-specific mutagenesis (Herlitze S. and Koenen M. (1990). A general and rapid mutagenesis method using polymerase chain reaction. Gene, 91, 143-147). The mutagenesis primer for preparing the T537M-α3 subunit had the following sequence (SEQ ID NO 7):
5'-CGACGCATGGCGAACATCCGCAGTCT-3'

The mutagenesis primer for preparing the T537V-α3 subunit had the following sequence (SEQ ID NO 8):
5'-CGACGCGTCGCGAACATCCGCAGTCT-3'

First, a PCR of pc3-bolf was carried out using the mutagenesis primer and the counterprimer #1817 (5'-TTGGCTG-CAGCTATTATGGCTTCTCGGCAG-3') (SEQ ID NO 9). A 100-μl PCR mixture comprised 10 ng of template DNA, 1.times.PCR buffer of Taq polymerase incl. 1.5 mM of $MgCl_2$, 200 μm of dNTPs, 1 U of Taq polymerase and in each case 150 ng of the two primers. The PCR conditions were as follows. 2 minutes of denaturation at 94.degree. C., followed by 25 cycles of in each case 45 s at 94.degree. C., 45 s at 46.degree. C., 45 s at 72.degree. C. The 404 bp fragment was purified and used together with the overlapping 666 bp Sma I/Pvu II restriction fragment as template for a further PCR. The flanking primers #1813 (5'-GTCGGATCCTCCACACT-CAAGAAAGTG-3') (SEQ ID NO 10) and #1817 were used for amplification. The PCR mixture had the same composition as indicated above, with the template used being 250 ng of the 1st PCR fragment and 10 ng of the restriction fragment instead of 10 ng of plasmid DNA. The PCR fragment was cleaved with BsrGI and substituted for the corresponding fragment in pc3-bolf. The sequence of the altered DNA section was checked by sequencing.

Isolation of cDNA Clones

The CRF receptor was cloned by carrying out a PCR of primary strand cDNA of rat hypophyses, using the primers #843 (5'-AGCGGGATCCACCATGGGACGGCGC-CCGCA-3') (SEQ ID NO 11) and #842 (5'-GGCCTG-GAGCTCACACTG-3') (SEQ ID NO 12). A 100 µl PCR mixture comprised 10 ng of primary strand cDNA, 1.times.PCR buffer for Taq polymerase incl. 1.5 mM of $MgCl_2$, 200 µm of dNTPs, 1 U of Taq polymerase and in each case 150 ng of the two primers. The PCR conditions were as follows. 2 minutes of denaturation at 94.degree. C., followed by 44 cycles of in each case 45 s at 94.degree. C., 45 s at 56.degree. C., 75 s at 72.degree. C. The 1271 bp fragment was cloned via BamHI and SacI in pBluescript SK.sup.—into (pBCRFR1). The sequence corresponds to the published sequence L25438 (Chang, C. P., Pearse R. V. II, O'Connel S. and Rosenfed M. G. (1993). Identification of a seven transmembrane helix receptor for corticotropin-releasing factor and sauvagine in mammalian brain. Neuron, 11, 1187-1195). The cDNA was subcloned into a pcDNA derivative for heterologous expression (pcCRFR1).

The plasmid $pcK_1M$ which contains the cDNA of the dopamine receptor from *Drosophila* (Gotzes F., Balfanz S. and Baumann A. (1994) Primary structure and functional characterization of a *Drosophila* dopamine receptor with high homology to human D1/5 receptors. Receptors Channels, 2, 131-141), was kindly provided by Dr. F. Gotzes.

Heterologous Expression in HEK 293 Cells and Preparation of Stable Cell Lines

Transient expression in HEK 293 cells was carried out as described in Baumann A., Frings S., Godde M., Seifert R. and Kaupp U. B. (1994) Primary structure and functional expression of a *Drosophila* cyclic nucleotide-gated channel present in eyes and antennae. EMBO J., 13, 5040-5050. For electrophysiological characterization, the cells were transferred to glass slides which had been coated with poly L-lysine, on the day after transfection. The electrophysiological studies were then carried out on the following day.

To prepare the stable cell lines, the cells were transfected in the same manner. Cell clones stably expressing the desired gene were selected by seeding 2.times.10.sup.4 cells on a 9 cm cell culture dish on the day after transfection. The cells were cultured for 20 days, with either G418 (800 µg/ml) (Calbiochem), Zeocin (100 µg/ml) (Invitrogen) or Hygromycin (100 µg/ml) (Invitrogen) being added to the cell culture medium. After 20 days, the cell clones expressing the resistance gene were isolated and expression of the CNG-channel gene or of the receptor gene was checked by Western blot analyses and functional studies (electrophysiological measurement and fluorescence-optical measurements). For Western blot analysis, the cells were homogenized in a lysis buffer (10 mM Hepes, 1 mM DTT and 1 mM ETDA at pH 7.4), 5.times.shock-frozen (in liquid nitrogen) and finally centrifuged at 55,000 rpm for 10 min. The membrane pellet was resuspended in dissolving buffer (150 mM NaCl, 1 mM $MgCl_2$, 20 mM Hepes at pH 7.5, 0.1 mM EGTA and 0.5% Triton X-100). In each case 3 µg of membrane proteins were separated by means of SDS-PAGE, transferred to Immobilon membranes and labeled with specific antibodies. The immunoreactivity was made visible with the aid of the ECL detection kit (Amersham).

Double-stable cell lines were prepared by continuing culturing a cell clone which stably expressed either the CNG-channel gene or the receptor gene and using it for transfecting the in each case other cDNA. The cell clones were selected and chosen as described above.

The fluorescence-optical measurements partly involved using cells which stably expressed a genetically modified α3 subunit of the CNG channel and transiently expressed the *Drosophila* dopamine receptor. For this purpose, cells of the stable T537M cell line were transfected as described by Baumann A., Frings S., Godde M., Seifert R., and Kaupp U. B. (1994) Primary structure and functional expression of a *Drosophila* cyclic nucleotide-gated channel present in eyes and antennae. EMBO J., 13, 5040-5050. On the day after transfection, the cells were seeded into a multiwell plate with 96 wells. The cell density per well was $2 \times 10^4$ cells.

For the fluorescence-optical measurement of stable cell lines, the cells were seeded into this multiwell plate with 96 wells one or two days before the measurement. The cell density was from 1.5 to $4 \times 10^4$ cells.

Electrophysiology

The genetically modified and the wild-type GNG channels were in each case heterologously expressed in HEK 293 cells (Baumann A., Frings S., Godde M., Seifert R., and Kaupp U. B. (1994) Primary structure and functional expression of a *Drosophila* cyclic nucleotide-gated channel present in eyes and antennae. EMBO J., 13, 5040-5050). The electrophysiological characterization of the genetically modified CNG channels was carried out using the patch clamp technique under voltage clamping conditions. The activation properties of the channels were determined and compared to those of the wild-type channels (FIGS. 1 to 4):

inside-out patches were excised from cells which stably expressed genetically modified or wild-type CNG channels. The bath solution containing different concentrations of cyclic nucleotides was used to flow over the membrane patches. Starting from a holding voltage of 0 mV, sudden voltage changes were applied to different test voltages between −100 mV and +100 mV at the patch with a step width of 20 mV. The currents were registered and analyzed using standard methods.

FIG. 1A depicts the current-voltage (IV) relationship of the depicts T537M-α3 subunit of the bovine CNG channel. The average currents (I) at different cAMP concentrations are plotted as a function of the voltage (Vm): 0 µm (filled circles), 0.3 µm (open circles), 1 µm (filled triangles), 3 µm (open triangles), 10 µm (filled squares), 30 µm (open squares), 100 µm (filled diamonds).

FIG. 1B shows the dependence of the average currents on cAMP concentration for the T537M-α3 subunit of the bovine CNG channel at a voltage of +100 mV (filled circles). The continuous line has been calculated according to the Hill equation $I=(I_{max}-I_{min})c^n/(K^n+c^n)+I_{min}$ (I: current; $I_{max}$: maximum current; $I_{min}$: minimum current; $K_{1/2}$: concentration at which half-maximum activation of the channels occurs; n: Hill coefficient; c: cAMP concentration) with the following parameters: $I_{max}$=328 pA; $I_{min}$=24 pA; $K_{1/2}$=2.9 µm; n=2.4.

FIG. 1C depicts the normalized dose-response relationship of the T537M-α3 subunit of the bovine CNG channel (continuous line) and that of the wild-type bovine α3 subunit (dotted line) at +100 mV. The continuous and dotted lines have been calculated according to the normalized Hill equation I.sub.norm.=$c^n/(c^n+K^n)$ with the following averaged parameters: (continuous line: $K_{1/2}$=2.7 μm; n=2.4; dotted line: $K_{1/2}$=80 μm; n=2.0).

Figure 2A:
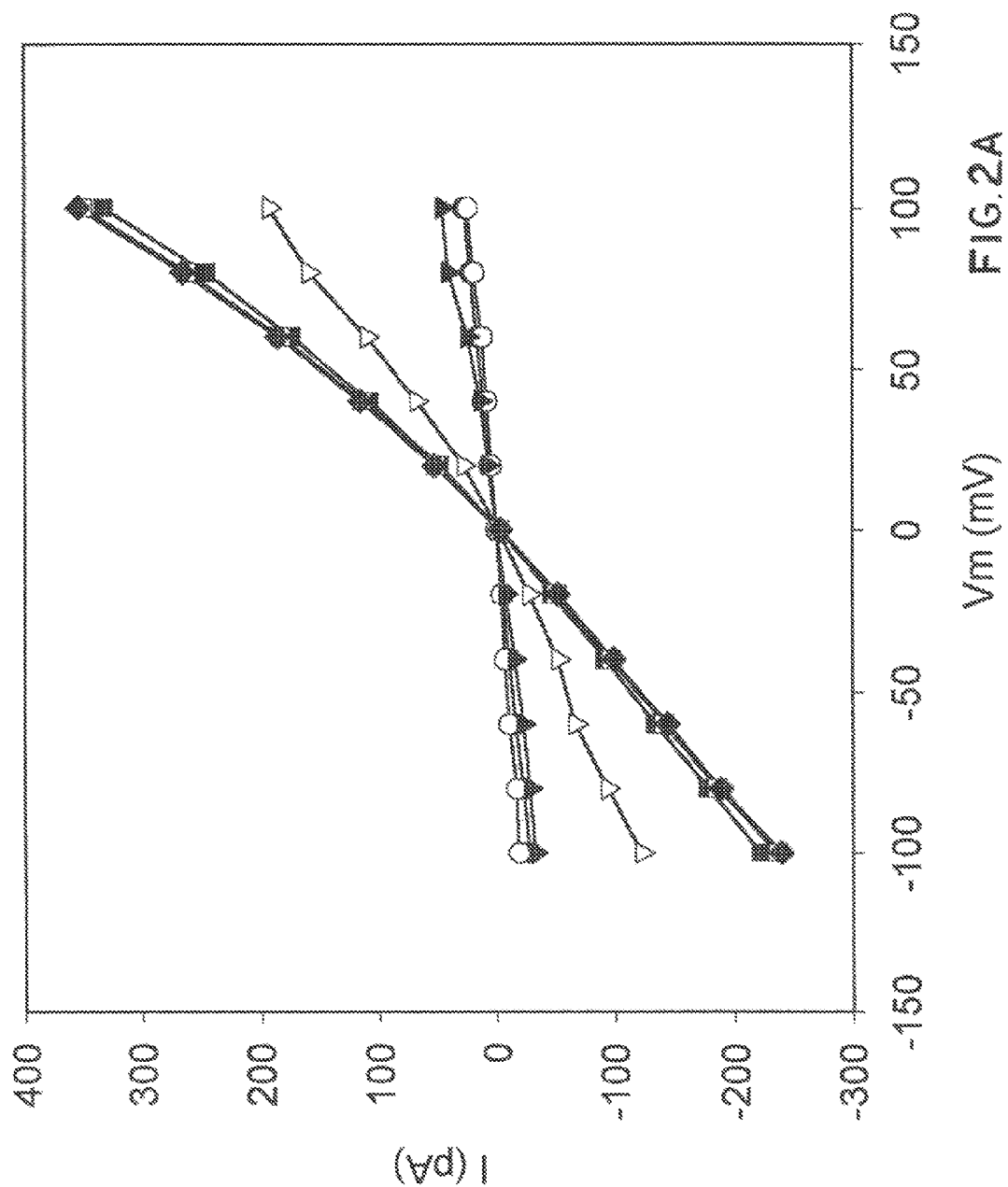

FIG. 2A depicts the current-voltage (IV) relationship of the heterologously expressed T537M-α3 subunit of the bovine CNG channel. The average currents (I) at different cGMP concentrations are plotted as a function of the voltage (Vm): 0 μm (filled circles), 1 μm (open circles), 3 μm (filled triangles), 10 μm (open triangles), 30 μm (filled squares), 100 μm (open squares), 300 μm (filled diamonds), 2,000 μm (open diamonds).

FIG. 2B shows the dependence of the average currents on cGMP concentration for the T537M-α3 subunit of the bovine CNG channel at a voltage of +100 mV (filled circles). The continuous line has been calculated according to the Hill equation I=$(I_{max}-I_{min})c^n/(K^n+c^n)+I_{min}$ (I: current; $I_{max}$: maximum current; $I_{min}$: minimum current; $K_{1/2}$: concentration at which half-maximum activation of the channels occurs; n: Hill coefficient; c: cGMP concentration) with the following parameters: $I_{max}$=167 pA; $I_{min}$=11 pA; $K_{1/2}$=12.0 μm; n=2.0.

FIG. 2C depicts the normalized dose-response relationship of the T537M-α3 subunit of the bovine CNG channel (continuous line) and that of the wild-type bovine α3 subunit (dotted line) at +100 mV. The continuous and dotted lines have been calculated according to the normalized Hill equation I.sub.norm.=$c^n/(c^n+K^n)$ with the following averaged parameters: (continuous line: $K_{1/2}$=14.9 μm; n=1.9; dotted line: $K_{1/2}$=1.6 μm; n=2.0).

Figure 3A:
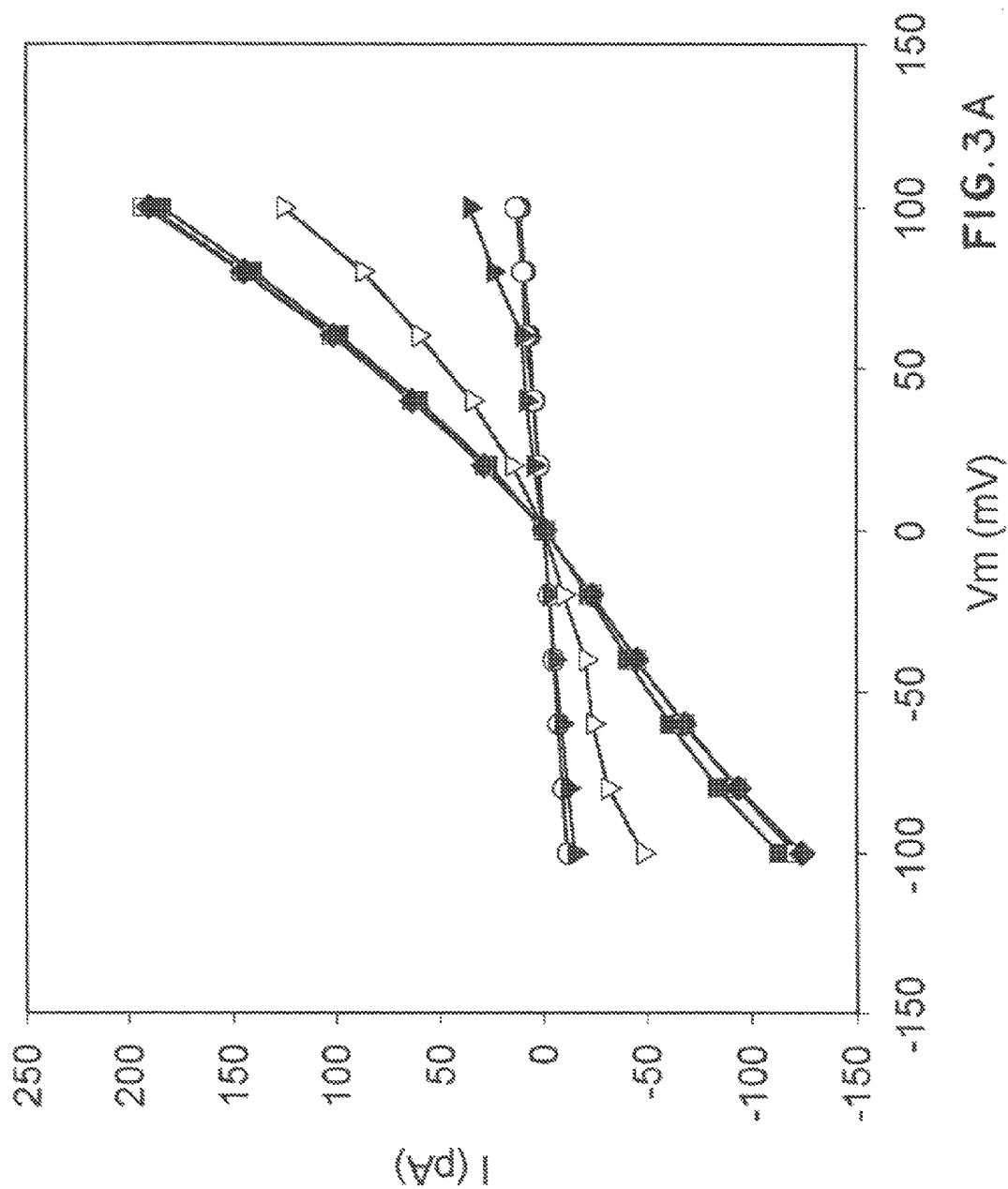

FIG. 3A depicts the current-voltage (IV) relationship of the heterologously expressed T537V-α3 subunit of the bovine CNG channel. The average currents (I) at different cAMP concentrations are plotted as a function of the voltage (Vm): 0 μm (filled circles), 3 μm (open circles), 10 μm (filled triangles), 30 μm (open triangles), 100 μm (filled squares), 300 μm (open squares), 1,000 μm (filled diamonds).

Figure 3B:
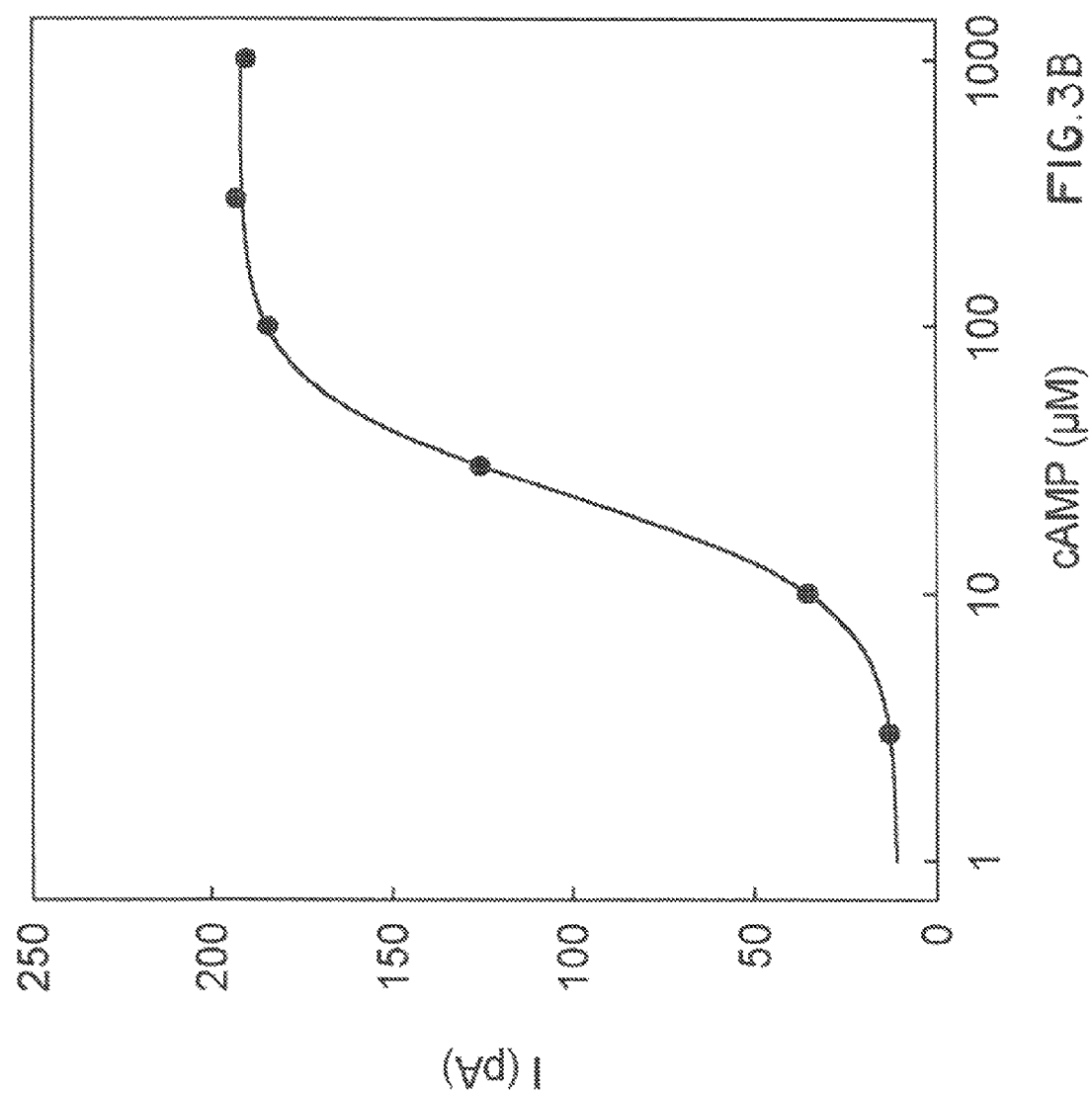

FIG. 3B shows the dependence of the average currents on cAMP concentration for the T537V-α3 subunit of the bovine CNG channel at a voltage of +100 mV (filled circles). The continuous line has been calculated according to the Hill equation I=$(I_{max}-I_{min})c^n/(K^n+c^n)+I_{min}$ (I: current; $I_{max}$: maximum current; $I_{min}$: minimum current; $K_{1/2}$: concentration at which half-maximum activation of the channels occurs; n: Hill coefficient; c: cAMP concentration) with the following parameters: $I_{max}$=181 pA; $I_{min}$=11 pA; $K_{1/2}$=23.4 μm; n=2.2.

FIG. 3C depicts the normalized dose-response relationship of the T537V-α3 subunit of the bovine CNG channel (continuous line) and that of the wild-type bovine α3 subunit (dotted line) at +100 mV. The continuous and dotted lines have been calculated according to the normalized Hill equation I.sub.norm.=$c^n/(c^n+K^n)$ with the following averaged parameters: (continuous line: K=34 μm; n=1.5; dotted line: $K_{1/2}$=80 μm; n=2.0).

Figure 4A:
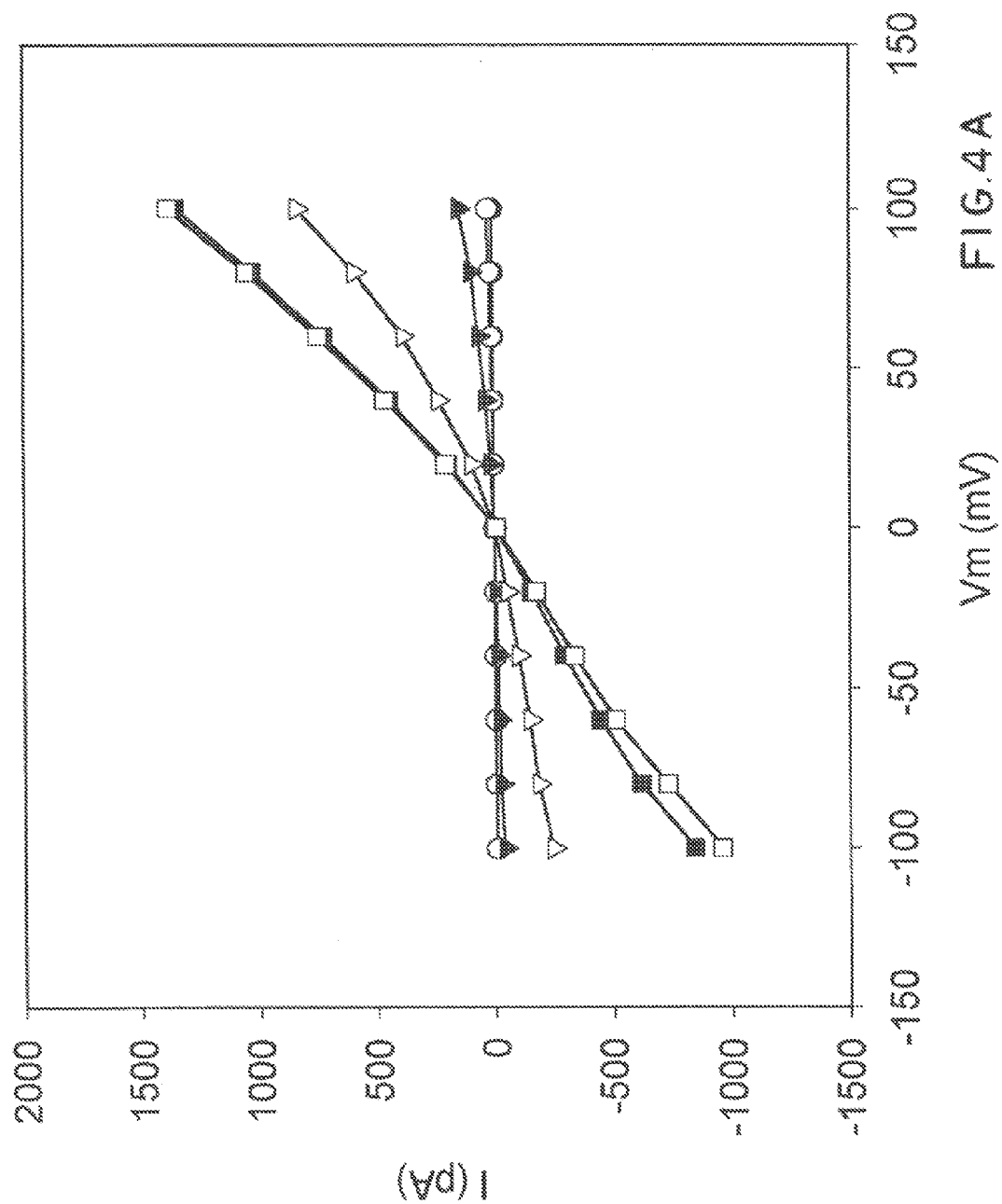

FIG. 4A depicts the current-voltage (IV) relationship of the heterologously expressed T537V-α3 subunit of the bovine CNG channel. The average currents (I) at different cGMP concentrations are plotted as a function of the voltage (Vm): 0 μm (filled circles), 30 μm (open circles), 100 μm (filled triangles), 300 μm (open triangles), 1,000 μm (filled squares), 2,000 μm (open squares).

FIG. 4B shows the dependence of the average currents on cGMP concentration for the T537V-α3 subunit of the bovine CNG channel at a voltage of +100 mV (filled circles). The continuous line has been calculated according to the Hill equation I=$(I_{max}-I_{min})c^n/(K^n+c^n)+I_{min}$ (I: current; $I_{max}$: maximum current; $I_{min}$: minimum current; $K_{1/2}$: concentration at which half-maximum activation of the channels occurs; n: Hill coefficient; c: cGMP concentration) with the following parameters: $I_{max}$=1 389 pA; $I_{min}$=13 pA; $K_{1/2}$=255.2 μm; n=2.2.

Figure 4C:
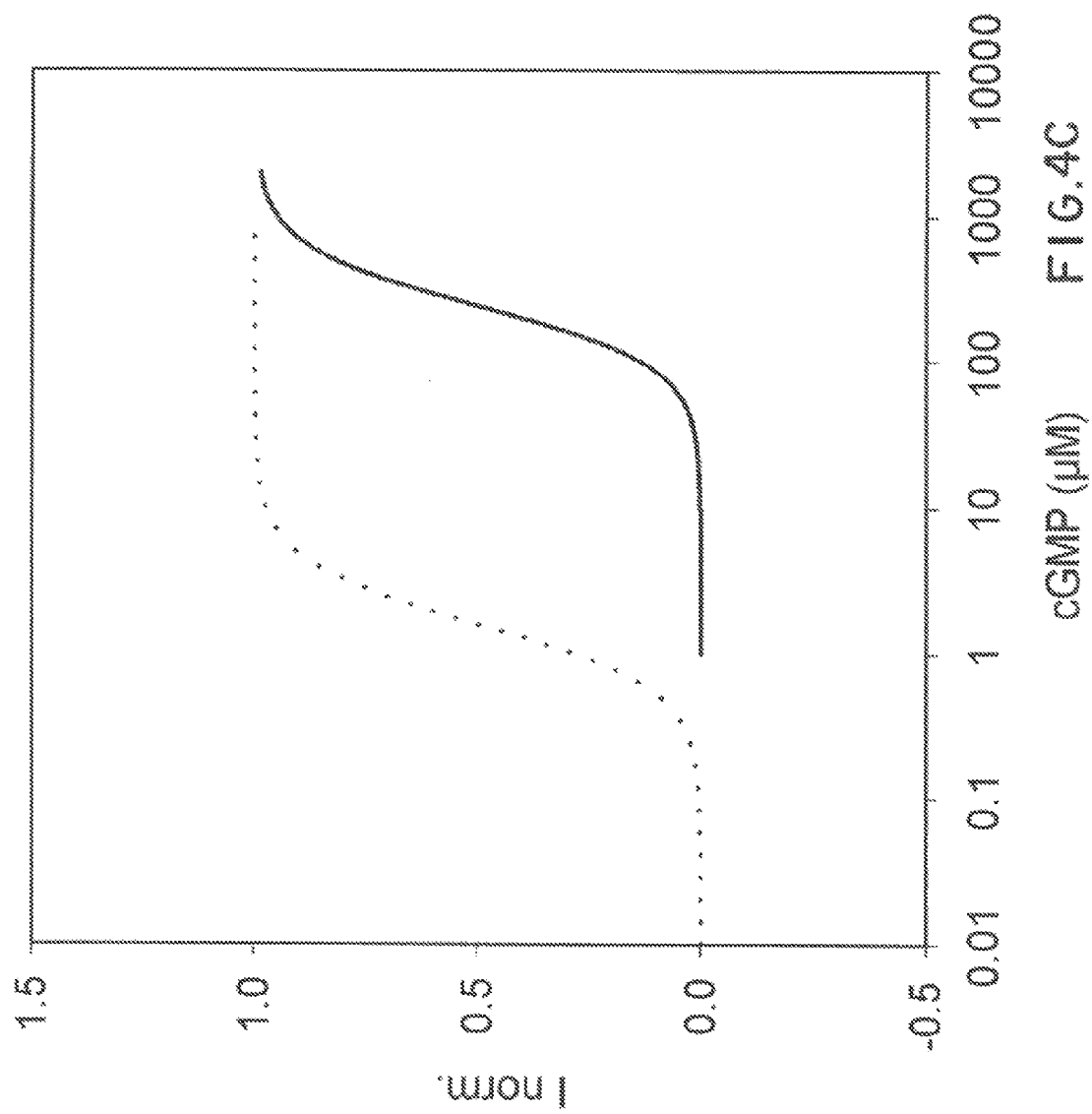

FIG. 4C depicts the normalized dose-response relationship of the bovine T537V-α3 subunit (continuous line) and that of the wild-type bovine α3 subunit (dotted line) at +100 mV. The continuous and dotted lines have been calculated according to the normalized Hill equation I.sub.norm.=$c^n/(c^n+K^n)$ with the following averaged parameters: (continuous line: K=241 μm; n=2.1; dotted line: $K_{1/2}$=1.6 μm; n=2.0).

FLUORESCENCE-OPTICAL MEASUREMENTS

The fluorimetric measurements of intracellular $Ca^{2+}$ concentrations were carried out in multiwell plates with 96 wells (FIG. 5A-5G). The cells were loaded with the $Ca^{2+}$-sensitive fluorescent dye Fluo-4 one hour before the measurement. The loading solution contained 120 mM of NaCl, 3 mM of KCl, 50 mM of glucose, 10 mM of Hepes (pH 7.4), 3 mM of $MgCl_2$ and 4 μm of Fluo4-AM (molecular probes). The measuring solution contained 120 mM of NaCl, 3 mM of KCl, 50 mM of glucose, 10 mM of Hepes (pH 7.4) and 3 mM of $CaCl_2$. The time course of the change in fluorescence intensity after application of agonists, antagonists, enzyme activators or enzyme inhibitors was registered using a fluorescence reader (FLUOstar, BMG-Labtechnologies). The excitation wavelength was 485 nm. The emission wavelength was 520 nm.

EXAMPLE 5

FIG. 5A depicts the fluorimetrically measured change in intracellular $Ca^{2+}$ concentration in cells transiently expressing the *Drosophila* dopamine receptor (DR) (Gotzes F., Balfanz S., and Baumann A. (1994) Primary structure and functional characterization of a *Drosophila* dopamine receptor with high homology to human D1/5 receptors. Receptor Channels, 2, 131-141) and stably expressing the T537M mutant of the α3-CNG channel. The time course of fluorescence intensity (RFU: relative fluorescence unit) after stimulation of the cells with different concentrations of the agonist dopamine is shown. The arrow marks the point in time at which the cells were stimulated with dopamine. The dopamine-induced activation of the dopamine receptor first leads in the cell to activation of a stimulatory G protein and finally to activation of an adenylate cyclase which synthesizes cAMP. Binding of cAMP opens CNG channels and $Ca^{2+}$ ions flow into the cell. The speed and extent of the change in $Ca^{2+}$ concentration depend on the dopamine concentration. The dopamine concentration was 25 nM (filled circles), 50 nM (open circles), 400 nM (filled triangles) or 600 nM (open triangles). For comparison, cells which do not express the dopamine receptor were also stimulated with 25 nM dopamine (filled rectangles).

EXAMPLE 6

Figure 5B:
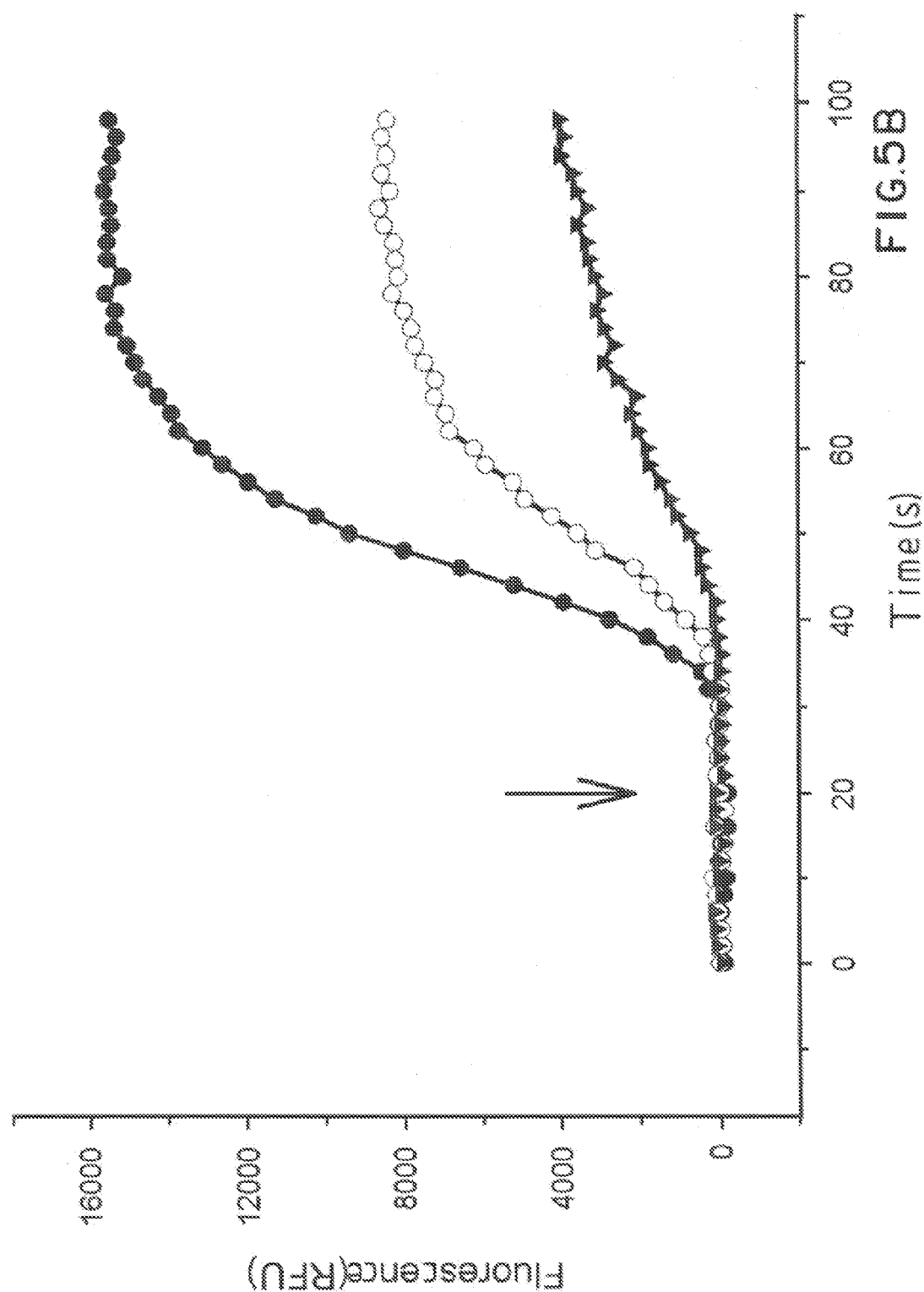
FIG. 5B is a graph plotting fluorescence against time showing the dose-dependent activation of the corticotropin-releasing factor (CRF) receptor by CRF in cells which stably co-express the CRF receptor and the T537M mutant of the a3-CNG channel.

FIG. 5B depicts the fluorimetrically measured change in intracellular $Ca^{2+}$ concentration in cells which stably express both the corticotropin-releasing factor (CRF) receptor and the T537M mutant of the α3-CNG channel. The time course of fluorescence intensity after stimulation of the cells with the agonist CRF is shown. The arrow marks the time at which cells were stimulated with CRF. CRF-induced activation of the CRF receptor leads in the cell first to activation of a stimulatory G protein and finally to activation of the adenylate cyclase which synthesizes cAMP (see, for example: Eckart K., Radulovic J., Radulovic M., Jahn O., Blank T., Stiedl O., and Spiess J. (1999) Actions of CRF and its analogs. Curr. Med. Chem., 6, 1035-1053; Perrin M. H. and Vale W. W. (1999). Corticotropin releasing factor receptors and their ligand family. Ann. N.Y. Acad. Sci., 885, 312-328). Binding of cAMP opens CNG channels and $Ca^{2+}$ ions flow into the cell. The speed and extent of the change in $Ca^{2+}$ depend on the CRF concentration. The CRF concentration was 100 pM (filled triangles), 300 pM (open circles) or 1,000 pM (filled circles).

FIGS. 5A and 5B depict by way of example for two different GCRPs coupling to a stimulatory G protein that the method of the invention can be used to measure the action of agonists on these GCRPs with high sensitivity. The method is equally suitable for all other GCRPs coupling to stimulatory G proteins. The examples of FIGS. 5A and 5B also show that it is possible to express for the method of the invention the heterologously expressed proteins (genetically modified α subunit of the CNG channel and GCRP) both transiently and stably in the cells.

EXAMPLE 7

Figure 5C:
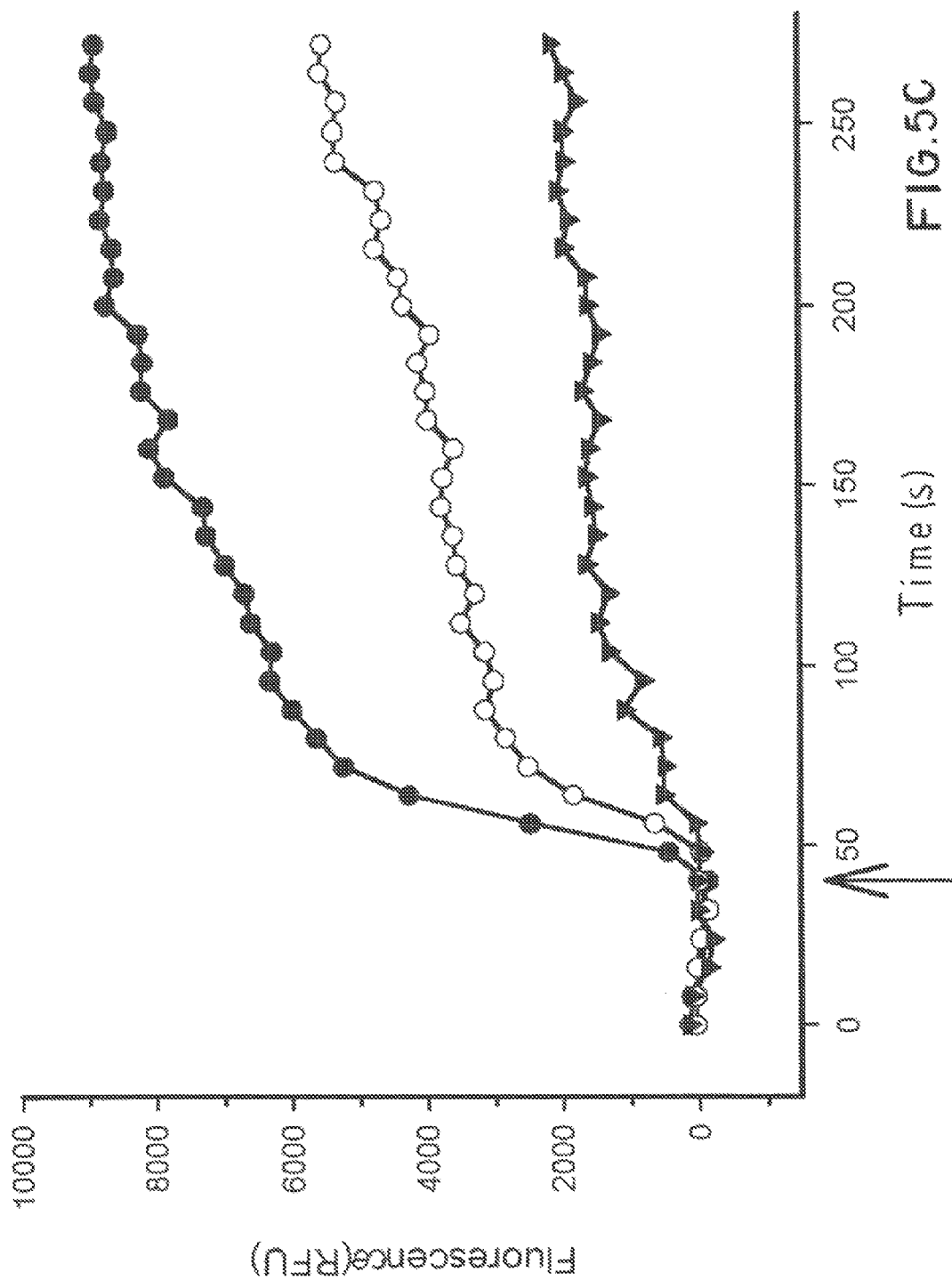
FIG. 5C is a graph plotting fluorescence against time showing the effectiveness of different antagonists to inhibit the activity of the CRF receptor in cells which stably co-express the CRF receptor and the T537M mutant of the a3-CNG channel.

FIG. 5C indicates that the method is suitable for quantitatively determining the effectiveness of different antagonists. Cells which stably express the corticotropin-releasing factor (CRF) receptor and the T537M mutants of the α3-CNG channel were treated with the helical antagonist 9-41 (Rivier J., Rivier C., and Vale W. W. (1984) Synthetic competitive antagonists of corticotropin-releasing factor: effect on ACTH secretion in the rat. Science, 224, 889-891), before being stimulated with CRF (1 nM). The time course of fluorescence intensity is shown. The arrow marks the point in time at which the cells were stimulated with CRF. With the same CRF concentration, the speed and extent of the change in $Ca^{2+}$ depend on the concentration of the antagonist. The concentration of the antagonist was 0 nM (filled circles), 10 nM (open circles) or 100 nM (filled triangles).

EXAMPLE 8

Figure 5D:
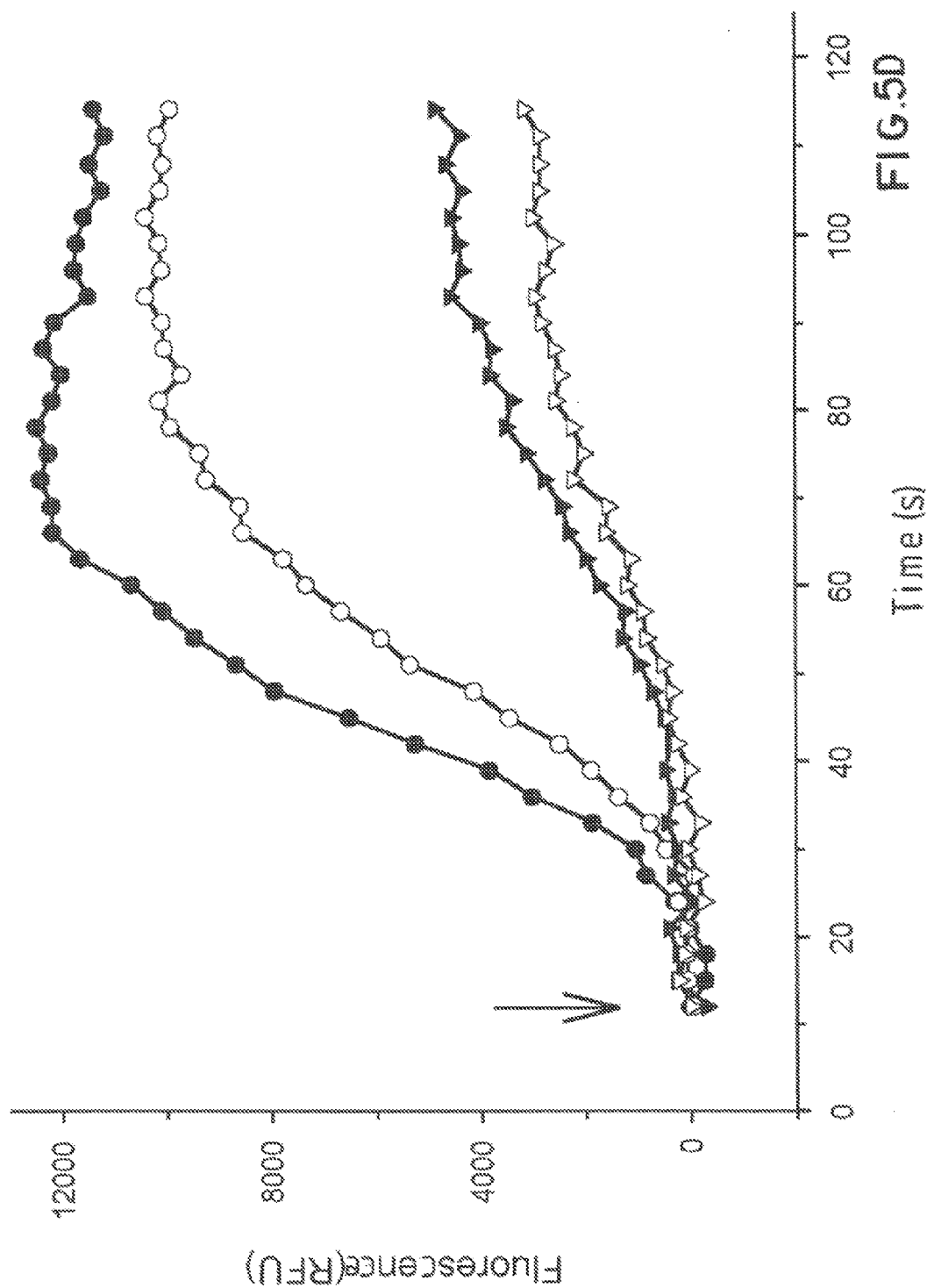
FIG. 5D is a graph plotting fluorescence against time showing the dose-dependent activation of the endogenous particular adenylate cyclase (AC) by its activator forskolin in cells which stably express the T537M mutant of the a3-CNG channel.

FIG. 5D indicates that the method is suitable for measuring the effectiveness of particular enzyme activators. The effect of an activator of adenylate cyclase (AC) on the change in intracellular $Ca^{2+}$ concentration is shown. Cells which stably express the T537M mutants of the α3-CNG channel were stimulated with different concentrations of the AC activator forskolin. The time course of fluorescence intensity is shown. The arrow marks the point in time at which the cells were stimulated with forskolin. Forskolin directly activates the adenylate cyclase endogenous to these cells (Seamon K. B. and Daly J. W. (1981) Forskolin: a unique diterpene activator of cyclic AMP-generating systems. J. Cyclic Nucleotide Res., 7, 201-224).

The rate and extent of the change in intracellular $Ca^{2+}$ concentration depend on the concentration of the AC activator. The forskolin concentration was 0.5 μm (open triangles), 0.75 μm (filled triangles), 2 μm (open circles) or 4 μm (filled circles).

EXAMPLE 9

Figure 5E:
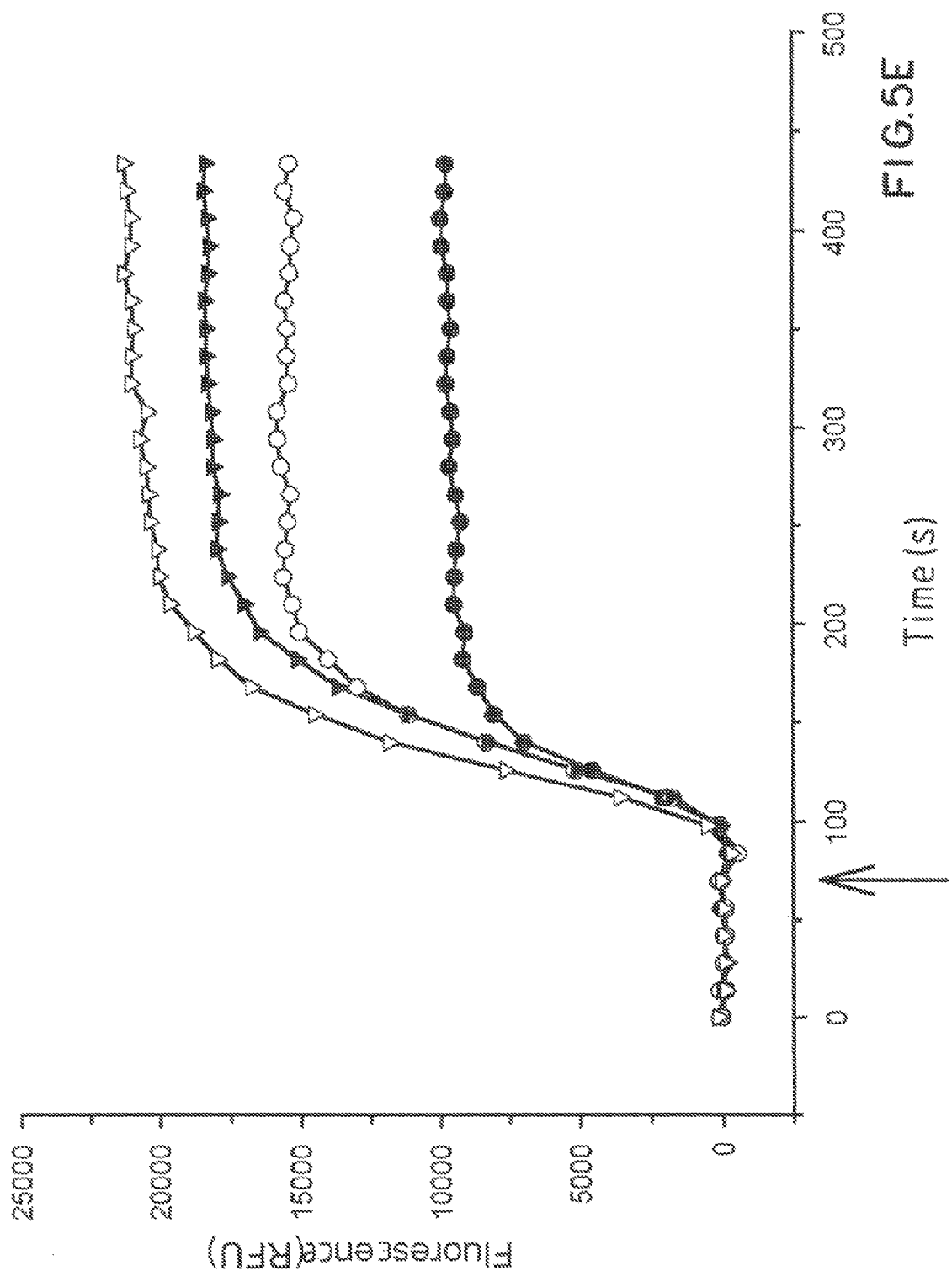
FIG. 5E is a graph plotting fluorescence against time showing the dose-dependent inhibition of the endogenous phosphodiesterase (PDE) by its inhibitor IBMX in cells which stably express the T537M mutant of the a3-CNG channel.

FIG. 5E indicates that the method is suitable for determining the effectiveness of particular enzyme inhibitors. The effect of a phosphodiesterase (PDE) inhibitor on the forskolin-induced change in intracellular $Ca^{2+}$ concentration is shown. Cells which stably express the T537M mutants of the α3-CNG channel were first treated with different concentrations of the PDE inhibitor IBMX and then stimulated with 5 μm forskolin. The plot shows the time course of fluorescence intensity. The arrow marks the point in time at which the cells were stimulated with forskolin. The PDE inhibitor inhibits the activity of the endogenous PDEs and thereby reduces degradation of cAMP synthesized due to a stimulation of the endogenous AC. The extent of the change in intracellular $Ca^{2+}$ concentration depend on the concentration of the PDE inhibitor. The IBMX concentration was 0 μm (filled circles), 10 μm (open circles), 50 μm (filled triangles) or 100 μm (open triangles).

The example shows that the method is suitable for measuring sensitively the effectiveness of PDE inhibitors. It is possible to study inhibitors of endogenous PDEs but also inhibitors of heterologously expressed PDEs.

The method of the invention is also suitable for determining the activity of GCRPs coupling to the inhibitory G protein $G_i$. If GCRPs of this kind are activated, the cellular cAMP concentration is reduced because ACs are inhibited. For the method of the invention, the cells must first be stimulated to synthesize cAMP (e.g. by the AC activator forskolin), before the activity of agonists can then be measured. Simultaneous or sequential application of antagonists and agonists make it also possible to test the effectiveness of antagonists for such GCRP.

The method is analogously suitable for determining any substances capable of increasing or reducing the cAMP concentration in the cell in any way. The direct points of attack of these substances (e.g. GCRP or enzymes) may either be present endogenously in the cells or may be transiently or stably expressed in cells together with genetically modified CNG channels.

EXAMPLE 10

Figure 5F:
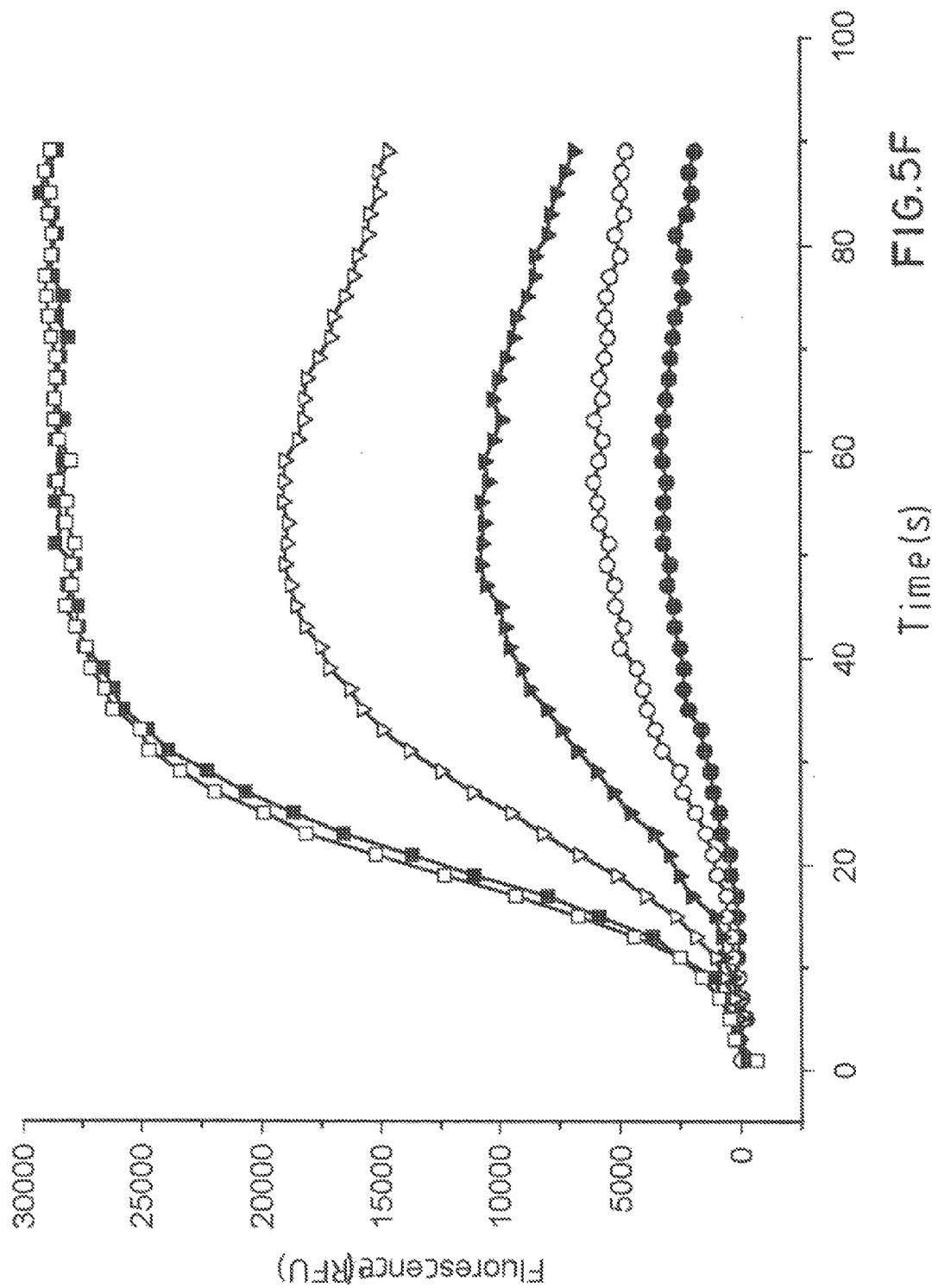
FIG. 5F is a graph plotting fluorescence against time showing the dose-dependent response activation of the endogenous adenosine receptor by its agonist adenosine in cells which stably express the T537M mutant of the a3-CNG channel.

FIG. 5F indicates that the method makes also quantitative analyses possible. Cells which stably express an endogenous adenosine receptor (Cooper J., Hill S. J. and Alexander S. P. (1997). An endogenous A2B adenosine receptor coupled to cyclic AMP generation in human embryonic kidney (HEK 293) cells, Br. J. Pharmacol., 122, 546-550) and the T537M mutant of the α3-CNG channel were stimulated with different concentrations of adenosine. The time course of fluorescence intensity is shown. The arrow marks the point in time at which the cells were stimulated with adenosine. The adenosine-induced activation of the adenosine receptor leads in the cell first to activation of a stimulatory G protein and finally to activation of the adenylate cyclase which synthesizes cAMP. Binding of cAMP opens CNG channels and $Ca^{2+}$ ions flow into the cell. The extent and rate of the change in intracellular $Ca^{2+}$ concentration depend on the adenosine concentration. The adenosine concentration was 0.9 μm (filled circles) and 1.5 μm (open circles), 3 μm (filled triangles), 6 μm (open triangles), 25 μm (filled rectangles) or 37.5 μm (open rectangles). FIG. 5G shows the dose-response relationship for adenosine. The rate of the change in fluorescence after addition of adenosine (initial rate) correlates with the adenosine concentration. The initial rates are plotted as a function of adenosine concentration. The continuous line has been calculated according to the Hill equation: initial slope=$a \times c^n/(K^n+c^n)$.sub.n (c=adenosine concentration; K: concentration at which the half-maximum initial rate is reached; n: Hill coefficient; a=maximum initial slope) with the following parameters: a=1 403 RFU/s; K=5.15 μm; n=2.16).

The $K_{1/2}$ value determined in this way agrees very well with the value of 5 μm indicated in the literature (Peakman M. C. and Hill S. J. (1994) Adenosine A2B receptor-mediated cyclic AMP accumulation in primary rat atrocytes, Br. J. Pharmacol., 111, 191-198).

EXAMPLE 11

FIG. 5H demonstrates the enormous improvement in sensitivity of the measuring system due to the use of the modified subunit of the α3-CNG channel. Cells which stably express the T537M mutant of the α3-CNG channel were stimulated with 3 μm adenosine to about half maximum (open circles) or with 25 μm adenosine to maximum (filled circles). The extent of the change in intracellular $Ca^{2+}$ concentration (fluorescence signal) was plotted as a function of time. The arrow marks the point in time at which the cells were stimulated with adenosine. Even after stimulation with half-maximum adenosine concentration a distinct increase in the fluorescence signal can be observed. In contrast, the cells which stably express the wild-type α3-CNG channel show no increase in the fluorescence signal, even after maximum stimulation with 25 μm adenosine (filled triangles). Cells which stably express the T537S mutant of the α3-CNG channel were also stimulated for comparison. After maximum stimulation of the endogenous adenosine receptor, only a very low increase in the fluorescence signal can be observed (filled rectangles).

The use of the genetically modified subunits of the invention considerably increases the sensitivity of the intracellular test system for studying the action of substances influencing the cAMP signal pathway, only thereby making cell sensitivity usable in practice. The signals are so large and the signal-to-noise ratio is so good that even quantitative analyses are possible. Suitable for preparing the cell lines of the invention are (not only HEK 293 cells) but in principle any eukaryotic cells which can be cultured in cell cultures. Both adherently growing cells and cells growing in suspensions may be used.

We claim:

1. A genetically modified cyclic nucleotide-gated ion channel (CNG channel) which comprises an α3 subunit from an animal which has been modified at a binding site for cyclic nucleotides in the position corresponding to threonine T537 in the bovine α3 subunit according to SEQ ID NO:2, wherein threonine is replaced by methionine or valine, so that it has higher sensitivity for cAMP and higher selectivity for cAMP than for cGMP in comparison with its wild type.

2. The genetically modified cyclic nucleotide-gated ion channel (CNG channel) defined in claim 1 which comprises an α3 subunit from a vertebrate or nonvertebrate animal.

3. The genetically modified vertebrate cyclic nucleotide-gated ion channel (CNG channel) defined in claim 2 wherein threonine is replaced by methionine.

4. The genetically modified vertebrate cyclic nucleotide-gated ion channel (CNG channel) defined in claim 2 wherein threonine is replaced by valine.

5. The genetically modified cyclic nucleotide-gated ion channel (CNG channel) defined in claim 1 which comprises an α3 subunit from a rat.

6. The genetically modified cyclic nucleotide-gated ion channel (CNG channel) defined in claim 1 which comprises an α3 subunit from a rat wherein threonine is replaced by methionine.

7. A method for preparing a genetically modified CNG channel which comprises an α3 subunit from an animal which has been modified at a binding site for cyclic nucleotides in the position corresponding to position T537 in the bovine α3 subunit according to SEQ ID NO:2 so that it has higher sensitivity for cAMP and higher selectivity for cAMP than for cGMP in comparison to its wild type, which comprises the step of replacing in the binding site of the α3 subunit, the amino acid corresponding to threonine 537 in the bovine α3 subunit according to SEQ ID NO: 2 with methionine or valine.

* * * * *